(12) United States Patent
Su et al.

(10) Patent No.: US 11,672,978 B2
(45) Date of Patent: Jun. 13, 2023

(54) SACRAL NERVE STIMULATION

(71) Applicant: Medtronic, Inc., Minneapolis, MN (US)

(72) Inventors: Xin Su, Plymouth, MN (US); David A. Dinsmoor, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 12 days.

(21) Appl. No.: 17/396,430

(22) Filed: Aug. 6, 2021

(65) Prior Publication Data

US 2021/0361942 A1 Nov. 25, 2021

Related U.S. Application Data

(63) Continuation of application No. 15/965,344, filed on Apr. 27, 2018, now abandoned.

(60) Provisional application No. 62/553,018, filed on Aug. 31, 2017, provisional application No. 62/583,254, (Continued)

(51) Int. Cl.
  *A61N 1/36* (2006.01)
  *A61N 1/05* (2006.01)
  *A61B 5/20* (2006.01)

(52) U.S. Cl.
  CPC ..... *A61N 1/36007* (2013.01); *A61N 1/36139* (2013.01); *A61N 1/36175* (2013.01); *A61B 5/202* (2013.01); *A61N 1/0514* (2013.01); *A61N 1/0553* (2013.01); *A61N 1/3606* (2013.01); *A61N 1/36031* (2017.08); *A61N 1/36171* (2013.01)

(58) Field of Classification Search
  CPC ............... A61B 5/202; A61N 1/36007; A61N 1/36139; A61N 1/36175; A61N 1/36031; A61N 1/0514; A61N 1/0553; A61N 1/3606; A61N 1/36171
  See application file for complete search history.

(56) References Cited

U.S. PATENT DOCUMENTS

| 5,416,469 A | 5/1995 | Colling |
| 5,984,854 A | 11/1999 | Ishikawa et al. |
| 6,400,982 B2 | 6/2002 | Sweeney et al. |

(Continued)

FOREIGN PATENT DOCUMENTS

| WO | 2010123704 A2 | 10/2010 |
| WO | 2011156288 A2 | 12/2011 |
| WO | 2015013749 A1 | 2/2015 |

OTHER PUBLICATIONS

Heesakkers et al., "A Novel Leadless, Miniature Implantable Tibial Nerve Neuromodulation System for the Management of Overactive Bladder Complaints," Neurourology and Urodynamics, vol. 37, No. 3, Mar. 2018, pp. 1060-1067.

(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

In some examples, a method including determining a chronaxie of evoked threshold motor responses from electrical stimulation delivered to a sacral nerve of a patient; and delivering, based on the determined chronaxie, electrical stimulation therapy, configured to treat a patient condition, to the sacral nerve having a pulse width at or near the identified chronaxie, wherein the delivered electrical stimu- (Continued)

lation is configured to inhibit contraction of at least one a bladder or bowel of the patient.

30 Claims, 14 Drawing Sheets

Related U.S. Application Data filed on Nov. 8, 2017, provisional application No. 62/583,814, filed on Nov. 9, 2017.

(56) References Cited

U.S. PATENT DOCUMENTS

| | | | |
|---|---|---|---|
| 6,678,548 | B1 | 1/2004 | Echauz et al. |
| 6,950,704 | B1 | 9/2005 | Bradley |
| 7,415,308 | B2 | 8/2008 | Gerber et al. |
| 7,580,741 | B2 | 8/2009 | Cazares et al. |
| 7,613,516 | B2 | 11/2009 | Cohen et al. |
| 7,764,996 | B2 | 7/2010 | Zhang et al. |
| 8,209,018 | B2 | 6/2012 | Osorio et al. |
| 8,447,413 | B2 | 5/2013 | Stone et al. |
| 9,555,246 | B2 | 1/2017 | Jiang et al. |
| 9,561,372 | B2 | 2/2017 | Jiang et al. |
| 9,855,423 | B2 | 1/2018 | Jiang et al. |
| 9,895,532 | B2 | 2/2018 | Kaula et al. |
| 10,092,762 | B2 | 10/2018 | Jiang et al. |
| 10,765,355 | B2 | 9/2020 | Nelson et al. |
| 2006/0020225 | A1 | 1/2006 | Gerber et al. |
| 2007/0100388 | A1 | 5/2007 | Gerber |
| 2007/0225616 | A1 | 9/2007 | Brown et al. |
| 2007/0255176 | A1 | 11/2007 | Rondoni et al. |
| 2007/0255346 | A1 | 11/2007 | Rondoni et al. |
| 2008/0058664 | A1 | 3/2008 | Mirro |
| 2009/0083070 | A1 | 3/2009 | Giftakis et al. |
| 2009/0270947 | A1* | 10/2009 | Stone ................. A61N 1/36082 607/59 |
| 2011/0040546 | A1 | 2/2011 | Gerber et al. |
| 2013/0007299 | A1 | 1/2013 | Su et al. |
| 2013/0072998 | A1* | 3/2013 | Su .......................... A61B 5/391 607/41 |
| 2013/0079841 | A1 | 3/2013 | Su et al. |
| 2013/0289446 | A1 | 10/2013 | Stone et al. |
| 2016/0136420 | A1 | 5/2016 | Brink et al. |
| 2017/0065821 | A1 | 3/2017 | Brink et al. |
| 2017/0080232 | A1* | 3/2017 | Torgerson ............ A61N 1/3615 |
| 2018/0214691 | A1 | 8/2018 | Famm et al. |
| 2019/0060647 | A1 | 2/2019 | Su et al. |
| 2019/0328303 | A1 | 10/2019 | Nelson et al. |
| 2020/0397361 | A1 | 12/2020 | Nelson et al. |
| 2021/0016091 | A1 | 1/2021 | Parker et al. |
| 2021/0121696 | A1 | 4/2021 | Parker et al. |

OTHER PUBLICATIONS

MacDiarmid et al., "Feasibility of a Fully Implanted, Nickel Sized and Shaped Tibial Nerve Stimulator for the Treatment of Overactive Bladder Syndrome with Urgency Urinary Incontinence," The Journal of Urology, vol. 201, May 2019, pp. 967-972.

Rogers et al., "Pivotal Study of Leadless Tibial Nerve Stimulation with eCoin® for Urgency Urinary Incontinence," The Journal of Urology, Mar. 8, 2021, 29 pp.

Ertekin et al., "Sacral Cord Conduction Time of the Soleus H-Reflex," Journal of Clinical Neurophysiology, vol. 13, No. 1, Feb. 1996, pp. 77-83.

Siegel et al., "Prospective Randomized Feasibility Study Assessing the Effect of Cyclic Sacral Neuromodulation on Urinary Urge Incontinence in Women," Female Pelvic Medicine & Reconstructive Surgery, vol. 24, No. 4, Jul./Aug. 2018, 5 pp.

Van Breda et al., "A New Implanted Posterior Tibial Nerve Stimulator for the Treatment of Overactive Bladder Syndrome: 3-Month Results of a Novel Therapy at a Single Center," The Journal of Urology, vol. 198, Jul. 2017, pp. 205-210.

Brink et al., "A Chronic, Conscious Large Animal Platform to Quantify Therapeutic Effects of Sacral Neuromodulation on Bladder Function," The Journal of Urology, vol. 194, No. 1, doi: 10.1016/j.juro.2015.01.109, Jul. 1, 2015, pp. 252-258.

Chantraine et al., "Motor Conduction Velocity in the Internal Pudendal Nerves," "Motor conduction velocity in the internal pudendal nerves," New Developments in Electromyography and Clinical Neurophysiology, vol. 2, 1973, (Applicant points out, in accordance with MPEP 609.04(a), that the year of publication, 1973, is sufficiently earlier than the effective U.S. filing date, so that the particular month of publication is not in issue.), pp. 433-438.

Goos et al., "New selective endoscopic sacral nerve root stimulation—an advance in the treatment of fecal incontinence" Neurogastroenterology & Motility, vol. 23, doi: 10.1111/j.1365-2982.2010.01607.,Sep. 2011, pp. e104-e109.

Henry et al., "Assessment of pelvic-floor disorders and incontinence by electrophysiological recording of the anal reflex," The Lancet, vol. 1 for 1978, No. 8066, Apr. 1, 1978, 4 pp.

Lee et al., "Comparison of Motor and Sensory Response of InterStim® for Overactive Bladder Syndrome," Female Pelvic Medicine & Reconstructive Surgery, vol. 19, No. 6, do: 10.1097/SPV. 0b013e3182a2954e, Nov./Dec. 2013, pp. 317-321.

Matzel et al., "Neuroanatomy of the Striated Muscular Anal Continence Mechanism," Implications for the Use of Neurostimulation. Diseases of the Colon & Rectum, vol. 33 No. 8, Aug. 1990, pp. 666-673.

McLennan, "The role of electrodiagnostic techniques in the reprogramming of patients with a delayed suboptimal response to sacral nerve stimulation," International Urogynecological Journal, Pelvic Floor Dysfunction, vol. 14, No. 2, doi: 10.1007/s00192-002-1029-9, Mar. 12, 2003, pp. 98-103.

Nowak et al., "Axons, but not cell bodies, are activated by electrical stimulation in cortical gray matter—II. Evidence from selective inactivation of cell bodies and axon initial segments." Springer-Verlag, Experimental Brain Research, vol. 118, No. 4, Feb. 1998, pp. 489-500.

Snooks et al., "Damage to the innervation of the voluntary anal and periurethral sphincter musculature in incontinence: an electrophysiological study," Journal of Neurology, Neurosurgery, and Psychiatry, vol. 47, May 2, 1984, pp. 1269-1273.

Su et al., "Optimization of Neuromodulation for Bladder Control in a Rat Cystitis Model," Neuromodulation: Technology at the Neural Interface, vol. 19, No. 1, doi: 10.1111/ner.12360, Jan. 2016, pp. 101-107.

Su et al., "Evaluation of Pulse-Width of Spinal Nerve Stimulation in a Rat Model of Bladder Micturition Reflex," Neuromodulation: Technology at the Neural Interface, vol. 20, DOI: 10.1111/ner. 12650, Jul. 20, 2017, pp. 793-798.

Grill Jr. et al., "The Effect of Stimulus Pulse Duration on Selectivity of Neural Stimulation," IEEE Transactions on Biomedical Engineering, vol. 43, No. 2, Feb. 1996, pp. 161-166.

Angel, "Central Neuronal Pathways and the Process of Anaesthesia," British Journal of Anaesthesia, vol. 71, Jul. 1993, pp. 148-163.

Cohen et al., "Predictors of Success for First State Neuromodulation: Motor Versus Sensory Response," American Urological Association, The Journal of Urology, vol. 175, No. 6, DOI:10.1016/ S0022-5347(06)00315-6, Jun. 2006, pp. 2178-2181.

Everaert et al., "Patient Satisfaction and Complications Following Sacral Nerve Stimulation for Urinary Retention, Urge Incontinence and Perineal Pain: a Multicenter Evaluation" International Urogynecology Journal, vol. 11, No. 4, DOI:10.1007/s001920070031, Feb. 2000, pp. 231-236.

Gorman et al., "The Effect of Stimulus Parameters on the Recruitment Characteristics of Direct Nerve Stimulation," IEEE Transactions on Biomedical Engineering, vol. 30, No. 7, Jul. 1983, pp. 407-414.

Hamdy et al., "Laterality effects of human pudendal nerve stimulation on corticoanal pathways: evidence for functional asymmetry," Gut, vol. 45, No. 1, Jul. 1999, pp. 58-63.

Hussain et al., "Neuromodulation for Lower Urinary Tract Dysfunction—An Update," The Scientific World Journal, vol. 7, Jun. 22, 2007, pp. 1036-1045.

(56) References Cited

OTHER PUBLICATIONS

Kiff et al., "Normal proximal and delayed distal conduction in the pudendal nerves of patients with idiopathic (neurogenic) fecal incontinence," Journal of Neurology, Neurosurgery, and Psychiatry, vol. 47, Jan. 1984, pp. 820-823.
Li et al., "Excitability Characteristics of the A- and C-Fibers in a Peripheral Nerve," Experimental Neurology, vol. 50, Jul. 24, 1975, pp. 67-79.
Maggi et al., "Suitability of urethane anesthesia for physiopharmacological investigations in various systems. Part 1: General considerations," Experientia, vol. 42, No. 2, Feb. 15, 1986, pp. 109-114.
Pedersen et al., "Anal sphincter responses after perianal electrical stimulation," Journal of Neurology, Neurosurgery, and Psychiatry, vol. 45, Jan. 1982, 770-773.
Peters, et al., "Effect of Sacral Neuromodulation Rate on Overactive Bladder Symptoms: A Randomized Crossover Feasibility Study," LUTS: Lower Urinary Tract Symptoms, vol. 5, DOI: 10.1111/luts.12000, May 2013, pp. 129-133.
Ranck Jr., "Which Elements are Excited in Electrical Stimulation of Mammalian Central Nervous System: A Review," Elsevier Scientific Publishing Company, Brain Research, vol. 98, May 1975, pp. 417-440.
Sangwan et al., "Unilateral Pudendal Neuropathy: Significance and Implications," Diseases of the Colon & Rectum, vol. 39, No. 3, Mar. 1996, pp. 249-251.
Schepens et al., "Neuromuscular blockade: what was, is and will be," Acta Anaesthesiologica Belgica, vol. 65, 2014, (Applicant points out, in accordance with MPEP 609.04(a), that the year of publication, 2014, is sufficiently earlier than the effective U.S. filing date, so that the particular month of publication is not in issue.), pp. 151-159.
Schmidt, "Clinical Value of Neurostimulation: A Urlogic Viewpoint," Female Urology, Chapter 58, Second Edition, Jan. 1996, pp. 643-655.
Siegel et al., "Three-year Follow-up Results of a Prospective, Multicenter Study in Overactive Bladder Subjects Treated with Sacral Neuromodulation" Female Urology, Urodynamics, Incontinence, and Pelvic Floor Reconstructive Surgery, vol. 94, http://dx.doi.org/10.1016/j.urology.2016.04.024, Apr. 28, 2016, pp. 57-63.
Snellings et al. "Effects of stimulation site and stimulation parameters on bladder inhibition by electrical nerve stimulation," BJU International, vol. 110, doi:10.1111/j.1464-410X.2011.10789.x, Aug. 2012, pp. 136-143.
Stern et al., "Chronaxie Measurements in Patterned Neuronal Cultures from Rat Hippocampus," PLoS One, vol. 10, No. 7, doi:10.1371/journal.pone.0132577, Jul. 17, 2015, 23 pp.
Su et al., "An excitatory role for peripheral EP3 receptors in bladder afferent function." American Journal of Physiology-Renal, vol. 295, doi:10.1152/ajprenal.90273.2008, Jun. 18, 2008, pp. F585-F594.
Su et al., "Effects of Opioids on Mechanosensitive Pelvic Nerve Afferent Fibers Innervating the Urinary Bladder of the Rat," The American Psychological Society, Journal of Neurophysiology, vol. 77, Mar. 1997, pp. 1566-1580.
Dinsmoor et al., "Chronaxie of Motor Responses to S3 Sacral Nerve Stimulation in Sheep," Society for Neuroscience (San Diego, CA), Nov. 12-16, 2016, 1 pp.
Su et al., "Electromyographic Responses Across Different Pulse-Widths of Sacral Neuromodulation in Sheep," Neuromodulation Journal, Neuromodulation: Technology at the Neural Interface, International Neuromodulation Society, Apr. 6, 2018, 6 pp.
Tsui et al., "The effects of general anaesthesia on nerve-motor response characteristics (rheobase and chronaxie) to peripheral nerve stimulation," Anaesthesia, vol. 69, No. 4, doi:10.1111/anae.12540, Apr. 2014, pp. 374-379.
Shariat et al., "Electrical Nerve Stimulators and Localization of Peripheral Nerves," NYSORA—The New York School of Regional Anesthesia, Sep. 19, 2013, 21 pp.

Grill Jr. et al. "Stimulus waveforms for selective neural stimulation," IEEE Engineering in Medicine and Biology Magazine, vol. 14, Issue 4,DOI: 10.1109/51.395310, Jul./Aug. 1995, pp. 375-385.
Ueyama et al., "Central Distribution of Efferent and Afferent Components of the Pudenal Nerve in Macaque Monkeys," Journal of Comparative Neurology, vol. 232, Oct. 5, 1984, pp. 548-556.
Zhang, et al., "Neural pathways involved in sacral neuromodulation of reflex bladder activity in cats," American Journal of Physiology-Renal, vol. 304, doi:10.1152/ajprenal.00334.2012., Jan. 2013, pp. F710-F717.
Cullheim et al. "Evidence for Direct Synaptic Interconnections Between Cat Spinal a-Mononeurons via the Recurrent Axon Collaterals: A Morphological Study Using Intracellular Injection of Horseradish Peroxidase," Brain Research, vol. 132, Dec. 1976, pp. 1-10.
Fowler et al., "Studies of the Latency of Pelvic Floor Contraction During Peripheral Nerve Evaluation Show That the Muscle Response is Reflexly Mediated," American Urological Association, Inc., The Journal of Urology, vol. 163, Mar. 2000, pp. 881-883.
Su et al., "Comparison of Active Stimulating Electrodes of Sacral Neuromodulation," Neuromodulation: Technology at the Neural Interface, Neuromodulation, vol. 20, DOI: 10.1111/ner.12710, Sep. 5, 2017, pp. 799-806.
Su et al., "Comparison of neural targets for neuromodulation of bladder micturition reflex in the rat," The American Psychological Society, American Journal of Physiology-Renal, vol. 303, doi:10.1152/ajprenal.00343.2012, Aug. 8, 2012, pp. F1196-F1206.
Su et al., "Neuromodulation in a rat model of the bladder micturition reflex," The American Psychological Society, American Journal of Physiology-Renal, vol. 302, doi:10.1152/ajprenal.00515.2011, Nov. 2, 2011, pp. F477-F486.
Su et al., "Quantification of effectiveness of bilateral and unilateral neuromodulation in the rat bladder rhythmic contraction model," BMC Urology, vol. 13, No. 34, http://www.biomedcentral.com/1471-2490/13/34, Jul. 18, 2013, 9 pp.
Szlavik et al., "The effect of stimulus current pulse width on nerve fiber size recruitment patterns," Elsevier, Medical Engineering & Physics, vol. 21, Jul. 20, 1999, pp. 507-515.
Tanagho et al., "Electrical Stimulation in the Clinical Management of the Neurogenic Bladder," State of the Art, The Journal of Urology, vol. 140, Dec. 1988, pp. 1331-1339.
Thor et al., "Organization of Afferent and Efferent Pathways in the Pudendal Nerve of the Female Cat," The Journal of Comparative Neurology, vol. 288, Apr. 27, 1989, pp. 263-279.
Ueyama et al., "Central Distribution of efferent and afferent components of the pudendal nerve in rat," Springer-Verlag, Anatomy and Embryology, vol. 177, Sep. 19, 1986, pp. 37-49.
Ueyama et al., "Central Distribution of Afferent and Efferent Components of the Pudendal Nerve in Cat," The Journal of Comparative Neurology, vol. 222, Jul. 18, 1983, pp. 38-46.
Wunderlich et al., "The Overlapping Innervation of the two Sides of the External Anal Sphincter by the Pudendal Nerves," Elsevier Biomedical Press, Journal of the Neurological Sciences, vol. 59, Oct. 18, 1982, pp. 97-109.
Yoshimura et al., "Histological and Electrical Properties of Rat Dorsal Root Ganglion Neurons Innervating the Lower Urinary Tract," Society for Neuroscience, The Journal of Neuroscience, vol. 23, No. 10, May 15, 2003, pp. 4355-4361.
Prosecution History for U.S. Appl. No. 15/965,344, dated Apr. 6, 2020 through Aug. 11, 2021, 95 pp.
Henry, "Neurophysiological assessment of the pelvic floor," Gut, vol. 29, Jan. 1, 1088, pp. 1-4.
Nowak et al., "Axons, but not cell bodies, are activated by electrical stimulation in cortical gray matter—I. Evidence from chronaxie measurements," Springer-Verlag, Experimental Brain Research, vol. 118, Aug. 5, 1997, pp. 477-488.
Decision on Appeal from U.S. Appl. No. 15/965,344 dated Sep. 30, 2022, 9 pp.
Reply Brief from U.S. Appl. No. 15/965,344, filed Oct. 11, 2021, 13 pp.

* cited by examiner

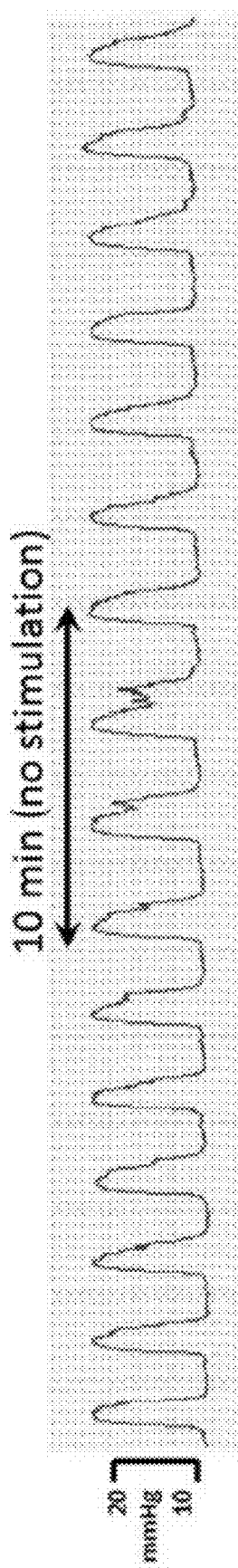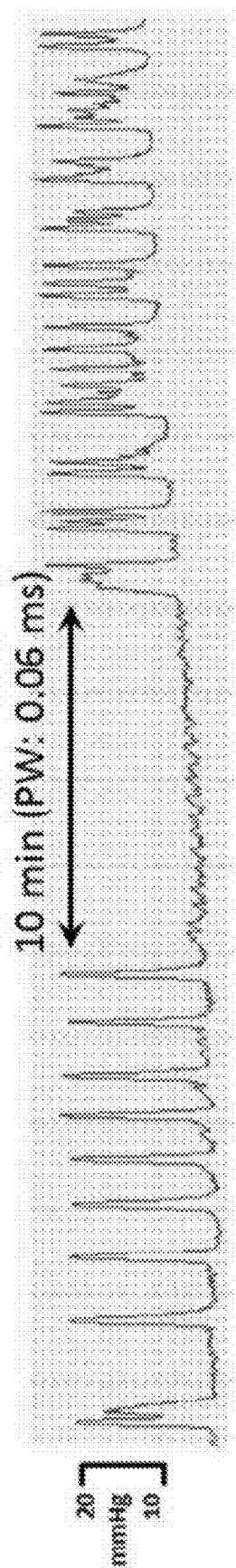
FIG. 13A
FIG. 13B

SACRAL NERVE STIMULATION

This application is a continuation of U.S. patent application Ser. No. 15/965,344, filed Apr. 27, 2018, which claims the benefit of U.S. Provisional Patent Application Nos. 62/553,018, filed Aug. 31, 2017, 62/583,254 filed Nov. 8, 2017, and 62/583,814, filed Nov. 9, 2017. The entire content of each of these applications is incorporated herein by reference.

TECHNICAL FIELD

The disclosure relates to medical devices and, more particularly, to medical devices that may be configured to deliver electrical stimulation.

BACKGROUND

Urinary and fecal incontinence (e.g., an inability to control bladder and bowel function, respectively) are problems that afflict people of all ages, genders, and races. Various muscles, nerves, organs and conduits within the pelvic floor cooperate to collect, store and release bladder and bowel contents. A variety of disorders may compromise urinary tract and bowel performance, and contribute to incontinence. Many of the disorders may be associated with aging, injury, or illness.

Urinary incontinence, such as, urgency incontinence, may originate from disorders of portions of the peripheral or central nervous system which control the bladder micturition reflex. Nerve disorders may also lead to overactive bladder activities and/or may prevent proper triggering and operation of the bladder. Furthermore, urinary incontinence may also result from improper communication between the nervous system and the urethra.

SUMMARY

Devices, systems, and techniques for managing urinary incontinence, fecal incontinence and/or other patient conditions using sacral nerve stimulation (also referred to as sacral neuromodulation or electrical stimulation of the sacral nerve) are described in this disclosure. In some examples, the disclosure relates to techniques for identifying efficient and preferred pulse widths for the electrical stimulation based on the chronaxie of threshold motor responses evoked by delivery of stimulation to a sacral nerve. For example, the chronaxie of electrical stimulation delivered to a sacral nerve site that evokes a threshold motor response may be identified for a patient. Electrical stimulation therapy that does not evoke a motor response but does inhibit contraction of at least one of the bladder or the bowel of the patient may then be delivered to the patient to treat a patient condition using a pulse width at or near the identified chronaxie. In this manner, the electrical stimulation therapy may be more efficient in terms of energy or power consumption compared to electrical stimulation therapy delivered to a patient with a greater pulse width.

In one example, the disclosure is directed to a method comprising determining a chronaxie of evoked threshold motor responses from electrical stimulation delivered to a sacral nerve of a patient; and delivering, based on the determined chronaxie, electrical stimulation therapy, configured to treat a patient condition, to the sacral nerve having a pulse width at or near the identified chronaxie, wherein the delivered electrical stimulation is configured to inhibit contraction of at least one a bladder or bowel of the patient.

In another example, the disclosure is directed to a medical device system comprising an electrical stimulation generator configured to deliver electrical stimulation to a sacral nerve site of a patient; and a processor configured to determine a chronaxie of evoked threshold motor responses from electrical stimulation delivered to a sacral nerve of a patient, and control the electrical stimulation generator to deliver, based on the determined chronaxie, electrical stimulation therapy configured to treat a patient condition to the sacral nerve having a pulse width at or near the identified chronaxie, wherein the delivered electrical stimulation is configured to inhibit contraction of at least one a bladder or bowel of the patient.

In another example, the disclosure is directed to a method comprising delivering electrical stimulation therapy configured to treat a patient condition to a sacral nerve having a pulse width of approximately 60 microseconds to approximately 80 microseconds, and an amplitude and frequency that does not evoke a motor response but does inhibit contraction of at least one a bladder or bowel of the patient.

The details of one or more aspects of the disclosure are set forth in the accompanying drawings and the description below.

BRIEF DESCRIPTION OF DRAWINGS

FIGS. 12A to 14B relate to a rat study that is described further below.

DETAILED DESCRIPTION

As described above, devices, systems, and techniques for managing incontinence (bladder incontinence and/or fecal incontinence) of a patient and/or other patient conditions via electrical stimulation of the sacral nerve are described in this disclosure. The electrical stimulation therapy may include delivery of electrical stimulation to one or more sacral nerve sites via a medical device. Such electrical stimulation may be used to modify pelvic function to treat various patient conditions (e.g., urinary incontinence and fecal incontinence) by inhibiting contraction of the bladder and/or bowel. Although the present disclosure describes application of electrical stimulation using an IMD, the devices, systems, and techniques of the present disclosure may also be implemented in an external medical device that applies electrical stimulation via implanted or external electrodes.

Examples of the disclosure are primarily described with regard to managing incontinence. In other examples, the electrical stimulation may be delivered to a patient to manage other patient conditions by inhibiting contraction of the bladder and/or bowel without evoking motor response, e.g., of the bladder and/or bowel.

A medical device may deliver sacral nerve stimulation therapy to inhibit bladder contraction and/or bowel contraction of a patient. Contraction may refer to muscle contractions within the bladder or bowel. In the case of the bladder, contraction may include contraction of the detrusor muscle or other muscle in the bladder of a patient. Such bladder contraction may result in a physiologically significant event, such as, e.g., the voiding of urine from the bladder (either voluntary or involuntary), or urge incontinence. Bladder contraction may include reflex contraction, or unwanted or pathological bladder contraction including both voiding and non-voiding contractions, such as, contractions causing urge incontinence. In the case of the bowel of a patient, bowel contraction may include bowel contraction that results in fecal voiding, either on a voluntary or involuntary basis. In some examples, the sacral nerve stimulation therapy delivered to the patient may inhibit bladder and/or bowel contraction by modulating nerve signals (e.g., sacral nerve signals). In some examples, the stimulation delivered to the patient to inhibit bladder contraction may define an intensity below an evoked motor response threshold of the stimulated nerve site, e.g., such that the stimulation does not result in a muscle evoked potential. The pulse width is an important parameter in determining the stimulation intensity required to activate nerve fibers with sacral nerve stimulation. As the pulse width increases, the minimum stimulation intensity needed for nerve excitation decreases.

Figure 6:
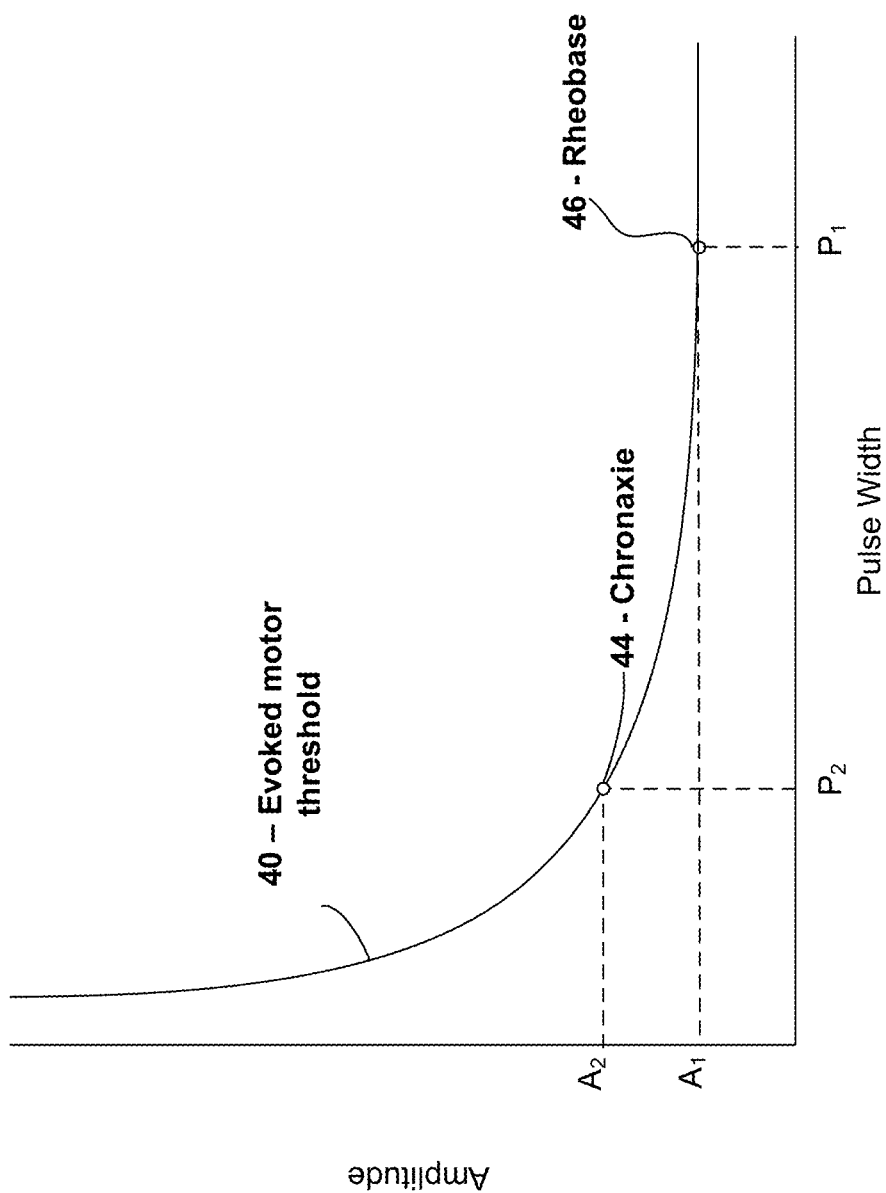
FIG. 6 is a plot of an example strength-duration curve for sacral nerve stimulation showing the chronaxie for an evoked motor response threshold.

In accordance with some examples of the disclosure, a medical device may deliver sacral nerve stimulation to a patient having a pulse width determined based on the chronaxie of evoked threshold motor responses from electrical stimulation of the sacral nerve site. The chronaxie refers to the minimum amount of time needed to stimulate a muscle or nerve site for electrical stimulation with an intensity (e.g., current amplitude or voltage amplitude) twice the value of the lowest intensity with indefinite pulse duration that stimulates the muscle or nerve (i.e., the rheobase). FIG. 6 is a strength-duration plot in terms of pulse width and amplitude showing an evoked motor response curve 40 for electrical stimulation of, e.g., a sacral nerve. The evoked motor response curve 40 represents the threshold intensity required to evoke a motor response with electrical stimulation for various different stimulation durations (e.g., pulse widths). For the plot in FIG. 6, amplitude Ai is the rheobase 46 and pulse width $P_2$ is the chronaxie 44.

In some examples, sacral nerve stimulation having a pulse width much greater than the chronaxie may be delivered to a patient to treat a patient disorder such as incontinence, e.g., by inhibiting contraction of the bladder and/or bowel with the sacral nerve stimulation. In some examples, such electrical stimulation may have a pulse duration of approximately 210 microseconds (μs). However, while such therapy may beneficially inhibit contraction of the bladder and/or bowel, it has been found that delivery of electrical stimulation with a pulse width at or near the chronaxie may provide for therapeutically effective stimulation comparable to electrical stimulation delivered at greater pulse widths but with reduced energy or power consumption.

As will be described further below, as one example, an optimal or otherwise preferential stimulus pulse width for sacral neuromodulation based on chronaxie of motor responses to third sacral foramen (S3) sacral nerve stimulation in sheep was identified in a sheep study. In the sheep study, the electromyography responses to sacral nerve stimulation with different stimulation pulse widths were randomly examined using variable intensities from 0.1 V to 10 V. The experimental data suggest that a similar motor response may be evoked in the external anal sphincter (EAS) at pulse widths much shorter (e.g., about 62 us to about 74 μs) than the 210 us used with sacral neuromodulation, in some cases. The use of shorter pulse widths translates directly to increased energy savings in a neurostimulator or other medical device configured to deliver electrical stimulation to a patient (compared to electrical stimulation having a greater pulse width) while still providing therapeutically effective stimulation to treat incontinence.

Additionally, as will be described below, the threshold difference between activation of different nerve fibers having different diameters is influenced by the pulse width of electrical stimulation. Shorter pulse widths will increase the differences in evoked motor threshold ($T_{mot}$) from different diameters of nerve fibers. The average recruited nerve fiber diameter decreases (~20%) when the stimulus pulse-width increases from 0.01 ms to 1 ms. The threshold difference between large and small nerve fibers increases along with the increase in the relative distance between the stimulating electrode and the nerve fibers. Thus, preferential activation of large nerve fibers over small fibers can be more pronounced with a shorter PW stimulation especially when the electrode is placed farther from the nerve roots. Accordingly, some examples of the disclosure employing relatively shorter pulse widths based on chronaxie of motor responses may provide for therapeutically effective stimulation while also reducing the likelihood of patient discomfort due to increased fiber selectivity preferential to larger fibers and reduced discomfort with short PW nerve stimulation.

Accordingly, some examples of the disclosure utilize a medical device configured to deliver electrical stimulation with a fixed pulse width of, e.g., about 60 μs to about 80 μs (e.g. 70 μs). The electrical stimulation may also have a fixed frequency of about 10 Hz, which may be the optimal or otherwise preferential frequency for neuromodulation of bladder function. One, and the only in some instances, adjustable parameter may be stimulation intensity, which would provide effective nerve stimulation and simple operation the medical device system. Such an example technique may be prescreened on chronaxie for patients who have no neuropathology conditions.

Some examples of the disclosure may include techniques in which the stimulation pulse width could be programed for neuromodulation based on individual patient's response to S3 nerve stimulation or other sacral nerve sites. For example, the chronaxie may vary based on condition of the nerve system of the patients and pulse width may be adjusted based on the response (e.g., motor response sensed via electromyography (EMG), patient sensation (e.g., tingle) and the like) to the delivered stimulation and may be also the outcome (readout) of diseases (looped control for example). This method may be useful for patients who have neuropathology conditions.

FIGS. 1-4 illustrate one example of a medical device system that may be employed to perform example techniques of this disclosure. However, other medical device systems may also employ the techniques of the disclosure.

Figure 1:
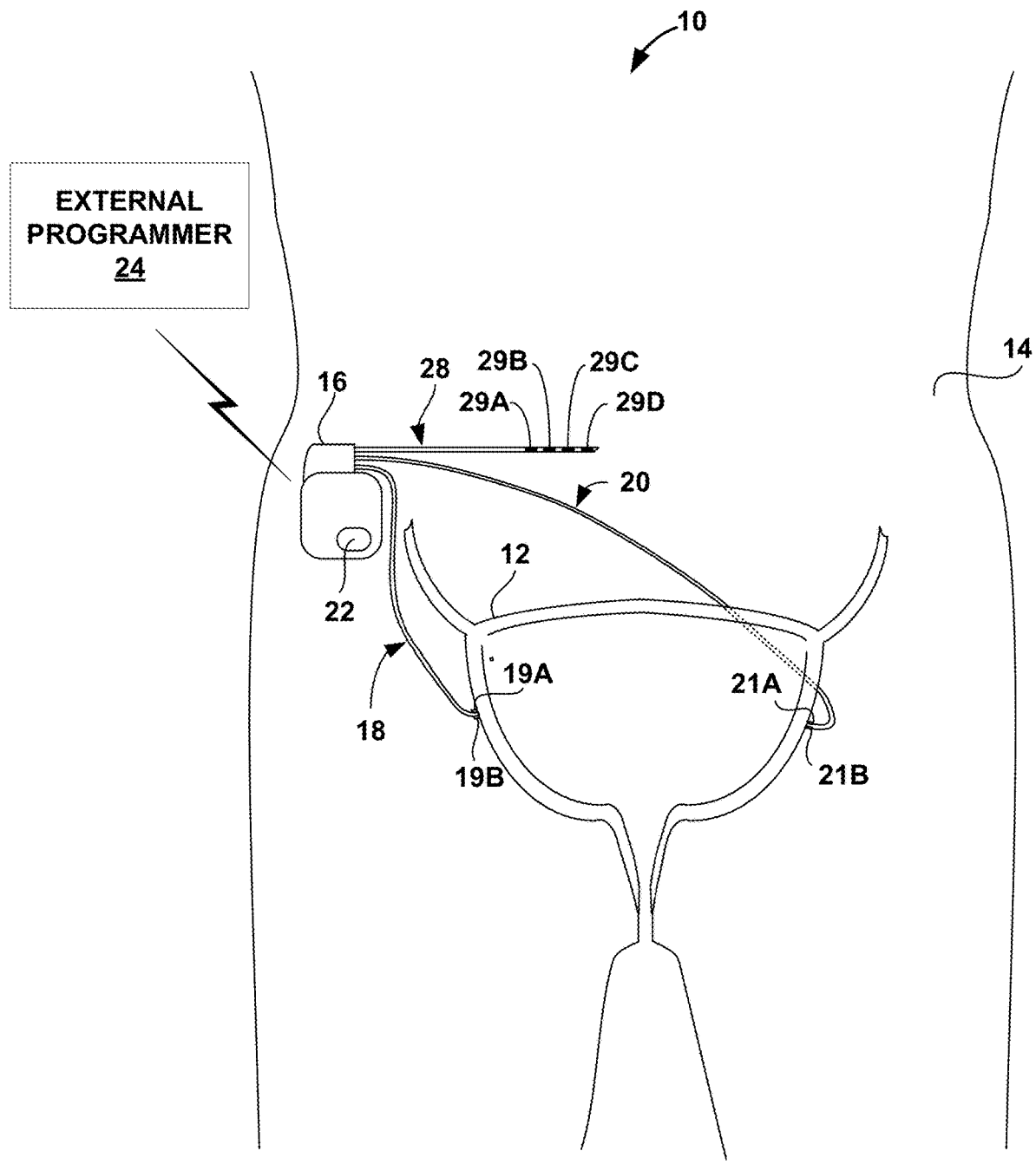
FIG. 1 is a conceptual diagram illustrating an example therapy system that delivers stimulation therapy to a patient to manage a patient condition such as, e.g., incontinence.

FIG. 1 is a conceptual diagram illustrating an example therapy system 10 that delivers electrical stimulation therapy to the sacral nerve of patient 14 to manage a patient condition of patient 14 (e.g., urinary incontinence or fecal incontinence). Therapy system 10 includes an implantable medical device (IMD) 16, which is coupled to leads 18, 20, and 28, sensor 22, and external programmer 24. IMD 16 may deliver the electrical stimulation therapy to a sacral nerve of patient 14 to inhibit bladder contractions or bowel contractions. As described herein, the pulse width of the electrical stimulation therapy may be selected based on the chronaxie determined for the electrical stimulation delivered to the sacral nerve of patient 14, e.g., using an electrical stimulation having a pulse width at or near the chronaxie and an amplitude and frequency that does not results in an evoked motor response but does inhibit bladder contractions or bowel contractions. For ease of description, system 10 is primarily described with regard to treatment of a patient condition, such as urinary incontinence, by delivering therapy to inhibit bladder contraction. However, system 10 may also be employed to treat other conditions, such as fecal incontinence by delivering therapy to inhibit bowel contraction.

IMD 16 provides electrical stimulation therapy to patient 14 by generating and delivering electrical stimulation signals to a target therapy site by lead 28 and, more particularly, via electrodes 29A-29D (collectively referred to as "electrodes 29") disposed proximate to a distal end of lead 28. For example, IMD 16 may deliver sacral nerve stimulation to patient 14 to inhibit bladder contraction following a bladder contraction, e.g., a contraction associated with a voiding event. In some examples, IMD 16 may delivery the stimulation to patient 14 based on, e.g., sensor data and/or patient input. As one example, IMD 16 may detect a bladder contraction based on sensor data and then deliver sacral nerve stimulation based on the detected bladder contraction. As another example, patient 14 may use external programmer 24 to provide patient input to IMD 16, e.g., indicating an increased probability of unintentional voiding, and IMD 16 may deliver the stimulation to patient 14 to inhibit bladder contraction based on the patient input.

IMD 16 may be surgically implanted in patient 14 at any suitable location within patient 14, such as near the pelvis. In some examples, the implantation site may be a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via a respective lead extension. Electrical conductors disposed within the lead bodies of leads 18, 20, and 28 electrically connect sense electrodes (not shown) and stimulation electrodes, such as electrodes 29, to a therapy delivery module (e.g., a stimulation generator) within IMD 16. In the example of FIG. 1, leads 18 and 20 carry electrodes 19A, 19B (collectively referred to as "electrodes 19") and electrodes 21A, 21B (collectively referred to as "electrodes 21"), respectively. As described in a further detail below, electrodes 19 and 21 may be positioned for sensing an impedance of bladder 12, which may decrease as the volume of urine within bladder 12 increases.

One or more medical leads, e.g., leads 18, 20, and 28, may be connected to IMD 16 and surgically or percutaneously tunneled to place one or more electrodes carried by a distal end of the respective lead at a desired sacral nerve site. In FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 21, 29 of leads 18, 20, 28, respectively, may be ring electrodes, segmented electrodes or partial ring electrodes. Segmented and partial ring electrodes each extend along an arc less than 360 degrees (e.g., 90-120 degrees) around the outer perimeter of the respective lead 18, 20, 28. In examples, one or more of leads 18, 20, 28 may be, at least in part, paddle-shaped (i.e., a "paddle" lead) and include pad electrodes positioned on a distal paddle surface.

In some examples, one or more of electrodes 19, 21, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 14 that results from the delivery of stimulation therapy.

The illustrated numbers and configurations of leads 18, 20, and 28 and electrodes carried by leads 18, 20, and 28 are merely exemplary. Other configurations, i.e., number and position of leads and electrodes, are possible. For example, IMD 16 may be coupled to additional leads or lead segments having one or more electrodes positioned at different locations in the pelvic region of patient 14. The additional leads may be used for delivering stimulation therapies to respective stimulation sites within patient 14 or for monitoring one or more physiological parameters of patient 14. In an example in which the target therapy sites for the stimulation therapies are different, IMD 16 may be coupled to two or more leads, e.g., for bilateral or multi-lateral stimulation. As another example, IMD 16 may be coupled to a fewer number of leads, e.g., just lead 28.

In some examples, IMD 16 may deliver stimulation therapy based on patient input. In some examples, patient 14 may provide patient input using external programmer 24 or by tapping over IMD 16 when IMD 16 includes a motion sensor that is responsive to tapping. Using programmer 24, patient 14 may provide input to IMD 16 that indicates an urge felt by the patient, a leakage incident experienced by the patient, an imminent voiding event predicted by the patient, or a voluntary voiding event to be undertaken by the patient. In this way, therapy system 10 provides patient 14 with direct control of stimulation therapy.

In the illustrated example of FIG. 1, IMD 16 determines an impedance through bladder 12, which varies as a function of the contraction of bladder 12, via electrodes 19 and 21 on leads 18 and 20, respectively. In the example shown in FIG. 1, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine bladder impedance based on the measurement of the transmitted electrical signal.

In the example four-wire arrangement shown in FIG. 1, electrodes 19A and 21A and electrodes 19B and 21B, may be located substantially opposite each other relative to the center of bladder 12. For example, electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 18 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced and the determined voltage.

In the example of FIG. 1, IMD 16 also includes a sensor 22 for detecting changes in the contraction of bladder 12. Sensor 22 may be, for example, a pressure sensor for detecting changes in bladder pressure, electrodes for sensing pudendal or sacral afferent nerve signals, or electrodes for sensing urinary sphincter EMG signals, or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples, IMD 16 may control the delivery of electrical stimulation based on input received from sensor 22. For example, IMD 16 may initiate the delivery of stimulation to inhibit the contract of bladder 12 when the sensor 22 indicates an increase in the probability of an involuntary voiding event of patient 14, such as when an increase in bladder pressure is detected by sensor 22.

In other examples, sensor 22 may comprise a patient motion sensor that generates a signal indicative of patient activity level or posture state. In some examples, IMD 16 controls the delivery of stimulation therapy to patient 14 based on sensed patient activity level or posture state. For example, a patient activity level that is greater than or equal to a threshold may indicate that there is an increase in urgency and/or an increase in the probability that an incontinence event will occur, and accordingly, IMD 16 may provide electrical stimulation based on the patient activity level.

As an additional example, patient 14 may be more prone to an incontinence event when patient 14 is in an upright posture state compared to a lying down posture state. Accordingly, in some examples, IMD 16 may control the delivery of electrical stimulation to patient based on the patient posture state determined based on a signal generated by sensor 22.

As another example, sensor 22 may generate a signal indicative of patient motion and IMD 16 or programmer 24 may determine whether patient 14 voluntarily voided based on a pattern in the patient motion signal associated with a voluntary voiding event alone or in combination with other sensed parameters (e.g., bladder impedance).

System 10 includes an external programmer 24, as shown in FIG. 1. In some examples, programmer 24 may be a wearable communication device, handheld computing device, computer workstation, or networked computing device. Programmer 24 may include a user interface that receives input from a user (e.g., patient 14, a patient caretaker or a clinician). The user interface may include a keypad and a display (e.g., an LCD display). The keypad may take the form of an alphanumeric keypad or a reduced set of keys associated with particular functions of programmer 24. Programmer 24 can additionally or alternatively include a peripheral pointing device, such as a mouse, via which a user may interact with the user interface. In some examples, a display of programmer 24 may include a touch screen display, and a user may interact with programmer 24 via the touch screen display. It should be noted that the user may also interact with programmer 24 and/or IMD 16 remotely via a networked computing device.

Patient 14 may interact with programmer 24 to control IMD 16 to deliver the stimulation therapy, to manually abort the delivery of the stimulation therapy by IMD 16 while IMD 16 is delivering the therapy or is about to deliver the therapy, or to inhibit the delivery of the stimulation therapy by IMD 16, e.g., during voluntary voiding events. Patient 14 may, for example, use a keypad or touch screen of programmer 24 to cause IMD 16 to deliver the stimulation therapy, such as when patient 14 senses that a leaking episode may be imminent. In this way, patient 14 may use programmer 24 to control the delivery of the stimulation therapy "on demand," e.g., when extra stimulation therapy is desirable.

Patient 14 may interact with programmer 24 to terminate the delivery of the stimulation therapy during voluntary voiding events or to modify the type of stimulation therapy that is delivered (e.g., to control IMD 16 to deliver stimulation therapy to help patient 14 voluntarily void in examples in which patient 14 has a urinary retention disorder). That is, patient 14 may use programmer 24 to enter input that indicates the patient will be voiding voluntarily. When IMD 16 receives the input from programmer 24, IMD 16 may suspend delivery the stimulation therapy for a predetermined period of time, e.g., two minutes, to allow the patient to voluntarily void, or switch to a different type of stimulation therapy to help patient 14 voluntarily void.

A user, such as a physician, technician, surgeon, electrophysiologist, or other clinician, may also interact with programmer 24 or another separate programmer (not shown), such as a clinician programmer to communicate with IMD 16. Such a user may interact with a programmer to retrieve physiological or diagnostic information from IMD 16. The user may also interact with a programmer to program IMD 16, e.g., select values for the stimulation parameter values of the therapy cycle with which IMD 16 generates and delivers electrical stimulation and/or the other operational parameters of IMD 16. For example, the user may use programmer 24 to retrieve information from IMD 16 regarding the contraction of bladder 12 and voiding events. As another example, the user may use programmer 24 to retrieve information from IMD 16 regarding the performance or integrity of IMD 16 or other components of system 10, such as leads 18, 20, and 28, or a power source of IMD 16.

In some examples, patient 14 or other user may interact with programmer 24 to instruct IMD 16 to identify a pulse width for the delivered electrical stimulation based on the determined chronaxie for the stimulation nerve site and/or assist IMD 16 in determining such a chronaxie, e.g., by providing input via programmer 24 identifying the motor threshold for stimulation at a given pulse width, e.g., based on patient 14 sensation of the activation by the electrical stimulation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In some examples, IMD 16 controls the delivery of stimulation to inhibit bladder contraction based on patient input from programmer 24 and/or sensor data (e.g., generated by sensor 22). Sensor data may include measured signals relating to urinary incontinence, e.g., bladder impedance, bladder pressure, pudendal or sacral afferent nerve signals, a urinary sphincter EMG, or any combination thereof. As another example, sensor data may include, and IMD 16 may deliver stimulation therapy in response to, measured signals relating to a patient activity level or patient posture state. In some instances, sensor data may be indicative of an increased probability of an occurrence of an involuntary voiding event.

Bladder contraction may be less likely immediately after a voiding event and/or the possibility of an involuntary voiding event may be relatively low immediately after a voiding event. Therefore, the delivery of stimulation to inhibit bladder contraction may not be necessary to prevent or at least minimize the possibility of an involuntary voiding event during the time period immediately following the occurrence of a voluntary or involuntary voiding event. In contrast, bladder contraction may be more likely as time passes since the last voiding event and/or the possibility of an involuntary voiding event may increase as time passes since the last voiding event. Accordingly, IMD 16 may delivery stimulation to inhibit bladder contraction only after a period of time has passed since the last voiding event. For example, IMD 16 may be configured to deliver electrical stimulation to inhibit bladder contraction only after fill level of the bladder is determined to be above a threshold level (e.g., some fill level associated with a high probability of an involuntary voiding event).

Figure 2:
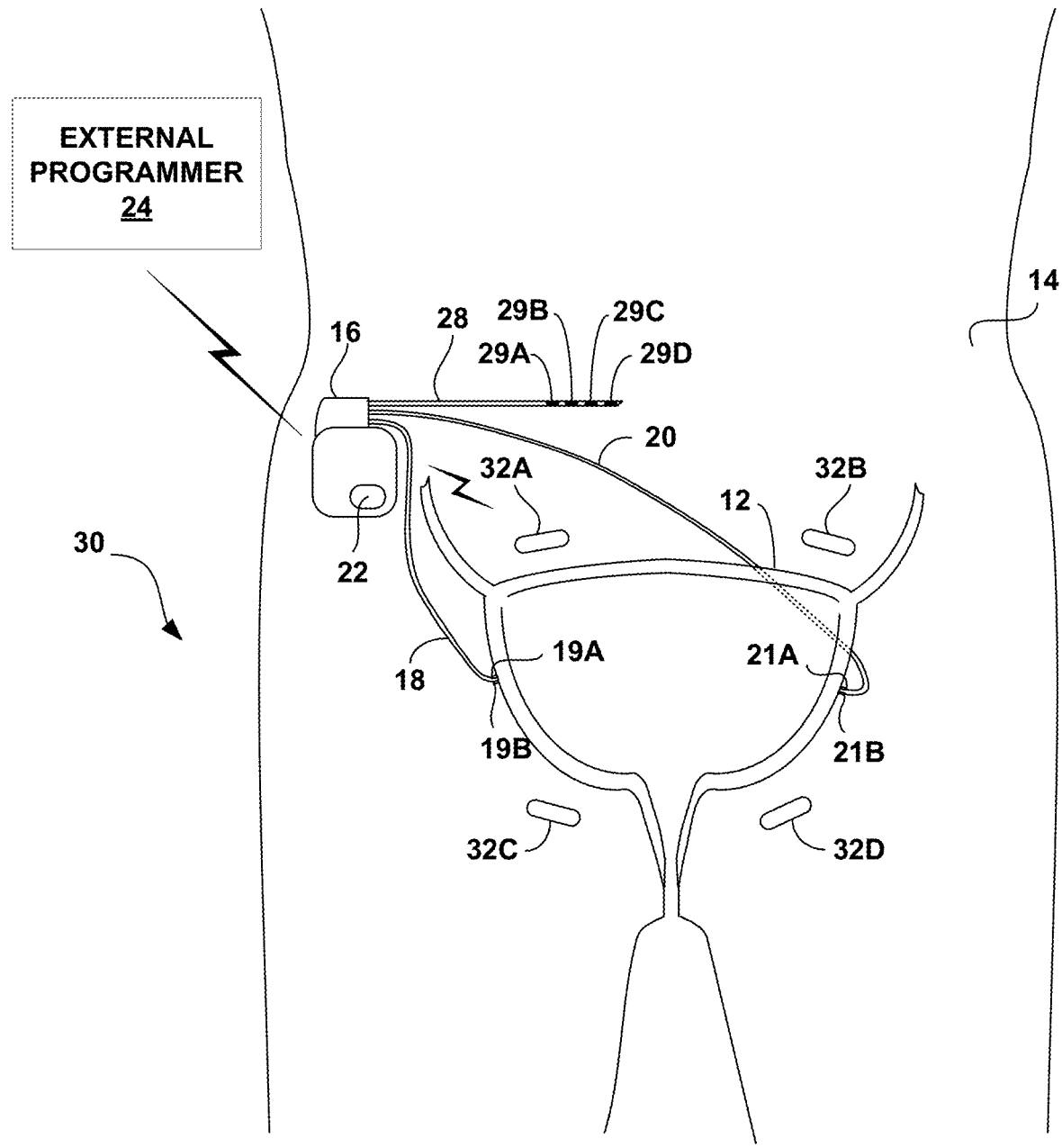
FIG. 2 is a conceptual diagram illustrating another example therapy system that delivers stimulation therapy to a patient to manage a patient condition such as, e.g., incontinence.

FIG. 2 is conceptual diagram illustrating another example therapy system 30 that delivers stimulation therapy to manage, e.g., urinary incontinence or other condition of patient 14. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 via one or more electrodes. Microstimulators 32 have a smaller size than IMD 16, and are typically leadless.

IMD 16 may deliver electrical stimulation therapies to patient 14 via microstimulators 32. For example, IMD 16 may communicate wirelessly with microstimulators 32 via wireless telemetry to control delivery of the stimulation therapies via microstimulators 32. In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible.

Systems 10 and 30 shown in FIGS. 1 and 2, respectively, are merely examples of therapy systems that may provide a stimulation therapy to manage urgency and/or urinary incontinence. Systems with other configurations of leads, electrodes, and sensors are possible. Additionally, in other examples, a system may include more than one IMD.

Figure 3:
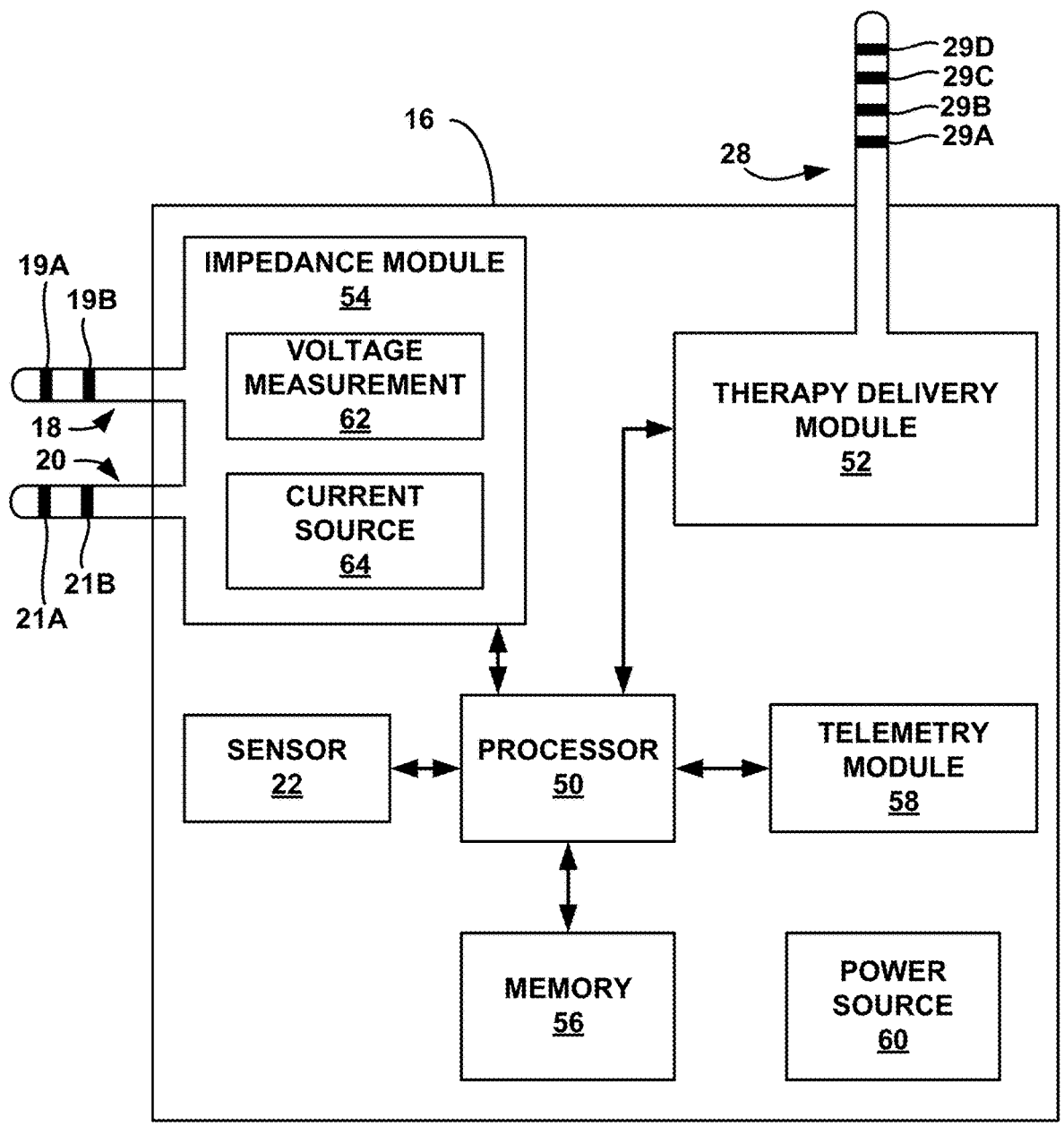
FIG. 3 is a functional block diagram illustrating an example configuration of the implantable medical device (IMD) of the systems shown in FIGS. 1 and 2.

FIG. 3 is a functional block diagram illustrating example components of IMD 16. In the example of FIG. 3, IMD 16 includes sensor 22, processor 50, therapy delivery module 52, impedance module 54, memory 56, telemetry module 58, and power source 60.

Therapy delivery module 52 generates and delivers electrical stimulation under the control of processor 50. In particular, processor 50 controls therapy delivery module 52 by accessing memory 56 to selectively access and load therapy programs into therapy delivery module 52. Therapy delivery module 52 generates and delivers electrical stimulation according to the therapy programs. In some examples, therapy delivery module 52 generates therapy in the form of electrical pulses. In other examples, therapy delivery module 52 may generate electrical stimulation in the form of continuous waveforms.

Patient 14 may provide patient input to IMD 16 using programmer 24 or another device, or directly via IMD 16. For example, patient 14 may provide patient input to IMD 16 using sensor 22 when sensor 22 includes a motion sensor that is responsive to tapping (e.g., by patient 14) on skin superior to IMD 16. When sensor 22 includes a motion sensor that is responsive to tapping, upon detecting the pattern of tapping that indicates a particular patient input, processor 50 may determine that the patient input was received.

Regardless of whether patient input is received from programmer 24 or other device, the patient input may indicate an urge felt by patient 14, a leakage incident experienced by patient 14, an imminent voiding event predicted by patient 14, a voluntary voiding event undertaken by patient 14 or other information that may affect the timing or intensity level of stimulation delivered by IMD 16.

In the example of FIG. 3, therapy delivery module 52 is electrically coupled to a single lead 28, and therapy delivery module 52 delivers electrical stimulation to a tissue site of patient 14 via selected electrodes 29A-29D carried by lead 28. A proximal end of lead 28 extends from the housing of IMD 16 and a distal end of lead 28 extends to one or more target therapy sites proximate a sacral nerve. In other examples, therapy delivery module 52 may deliver electrical stimulation with electrodes on more than one lead and each of the leads may carry one or more electrodes. The leads may be configured as axial leads with ring electrodes and/or paddle leads with electrode pads arranged in a two-dimensional array. Additionally, or alternatively, the leads may include segmented and/or partial ring electrodes. The electrodes may operate in a bipolar or multi-polar configuration with other electrodes, or may operate in a unipolar configuration referenced to an electrode carried by the device housing or "can" of IMD 16. In yet other examples, such as system 30 shown in FIG. 2 that includes microstimulators 32, processor 50 may act as a "master" module that controls microstimulators to deliver stimulation at target therapy sites. In other examples, however, one of microstimulators 32 may act as a master module or microstimulators 32 may be self-controlled.

In some examples, processor 50 controls therapy module 52 to deliver the stimulation therapy to patient 14 based on signals received from impedance module 54, sensor 22, or patient input received via telemetry module 58. In the example shown in FIG. 3, processor 50 monitors bladder impedance to detect bladder contractions based on signals received from impedance module 54. For example, processor 50 may determine an impedance value based on signals received from impedance module 54, and a particular impedance value may be associated with a bladder contraction (e.g., based on data obtained during a programming period). Therapy module 52 may deliver electrical stimulation therapy to patient 14 based on detection of bladder contraction using impedance module 54. For example, therapy module 52 may deliver electrical stimulation to inhibit bladder contraction in response to detection of an impedance value that indicates that the likelihood of a bladder contraction is increasing in order to address a possible increase likelihood of unintentional voiding. In other examples, therapy module 52 may deliver electrical stimulation to inhibit bladder contraction in response to detection of an impedance value (e.g., a low impedance value) that indicates that the bladder is filling in order to address a possible increase in the likelihood of unintentional voiding. In still other examples, a high impedance value may indicate that the bladder is empty, for example, after a voiding event.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processor 50 may periodically control current source 64 to, for example, source an electrical current signal through electrode 19A and sink the electrical current signal through electrode 21A. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processor 50 determines an impedance value from the measured voltage values received from voltage measurement circuitry 52.

Processor 50 may delivery stimulation to inhibit bladder contraction based on signals received from sensor 22 in addition to, or instead of, impedance module 54. In examples in which sensor 22 includes a pressure sensor, processor 50 may determine a bladder pressure value based on signals received from the pressure sensor. Processor 50 may determine whether contractions of bladder 12 are indicative an imminent incontinence event, for example, based on comparison of the sensed pressure to a pressure threshold that indicates an imminent event. For example, processor 50 may detect an imminent incontinence event when the sensed pressure is greater than the pressure threshold. Accordingly, in some examples, therapy delivery module 52, under control of processor 50, may deliver electrical stimulation to inhibit bladder contraction when sensed pressure is greater than the pressure threshold.

In examples in which sensor 22 includes a motion sensor, processor 50 may determine a patient activity level or posture state based on a signal generated by sensor 22. For example, processor 50 may determine a patient activity level by sampling the signal from sensor 22 and determining a number of activity counts during a sample period, where a plurality of activity levels are associated with respective activity counts. In one example, processor 50 compares the signal generated by sensor 22 to one or more amplitude thresholds stored within memory 56, and identifies each threshold crossing as an activity count.

Processor 50 may determine a patient posture state based on a signal from sensor 22 using any suitable technique. In one example, a posture state may be defined as a three-dimensional space (e.g., a posture cone or toroid), and whenever a posture state parameter value, e.g., a vector from a three-axis accelerometer of sensor 22 resides within a predefined space, processor 50 indicates that patient 14 is in the posture state associated with the predefined space.

Certain posture states or activity levels may be associated with a higher incidence of incontinence events. For example, patient 14 may have less control of the pelvic floor muscles when occupying an upright posture state or when patient 14 is in a highly active state (e.g., as indicated by a stored activity count or a threshold activity signal value). Thus, detection of these activity levels or posture states may be triggers for the delivery of stimulation therapy. For example, therapy delivery module 52 may, under control of processor 50, deliver electrical stimulation when sensed activity levels or patient posture indicates an increased probability that an incontinence event may occur.

The threshold values stored in memory 56 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on patient input, e.g., via external programmer 24. As an example, patient 14 may indicate, via programmer 24, when an involuntary voiding event takes place. When the patient input is received, processor 50 may determine an impedance value during the event or immediately prior to the event based on signals received from impedance module 54. A new threshold value may be determined using this impedance value. For example, the threshold value stored may be a running average of impedance values measured during involuntary voiding events.

In some examples, IMD 16 includes impedance sensing module 54 and not sensor 22, while in other examples IMD 16 includes sensor 22 but not impedance sensing module 54. Moreover, in some examples, sensor 22 and/or impedance sensing module 54 may be physically separate from IMD 16. Physically separate sensors may be useful in examples in which either sensor 22 and/or impedance sensing module 54 sense one or more physiological parameters at a location that is not accessible by IMD 16 or difficult to access by IMD 16.

Processor 50 may control therapy delivery module 52 to deliver stimulation therapy based on patient input received via telemetry module 58. Telemetry module 58 includes any suitable hardware, firmware, software or any combination thereof for communicating with another device, such as programmer 24 (FIG. 1). Under the control of processor 50, telemetry module 58 may receive downlink telemetry, e.g., patient input, from and send uplink telemetry to programmer 24 with the aid of an antenna, which may be internal and/or external. Processor 50 may provide the data to be uplinked to programmer 24 and the control signals for the telemetry circuit within telemetry module 58, and receive data from telemetry module 58.

Processor 50 may control telemetry module 58 to exchange information with medical device programmer 24. Processor 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

The processors described in this disclosure, such as processor 50 and processing circuitry in impedance module 54 and other modules, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. In some examples, the processing circuitry of impedance module 54 that determines an impedance based on a measured voltage and/or current of a signal may be the same microprocessor, ASIC, DSP, or other digital logic circuitry that forms at least part of processor 50.

Memory 56 stores instructions for execution by processor 50, in addition to therapy cycles. In some examples, memory 56 store patient parameter information, such as information generated by impedance module 54 and/or sensor 22. For example, information related to measured impedance and determined posture may be recorded for long-term storage and retrieval by a user, or used by processor 50 for adjustment of stimulation parameters, such as amplitude, pulse width, and frequency (e.g., pulse rate). Memory 56 may include separate memories for storing instructions, electrical signal information, programs, and other data.

In addition to the stimulation pulse widths described herein, example ranges of electrical stimulation parameters that may be used in the electrical stimulation therapy include amplitude (voltage amplitude or current amplitude) and frequency (e.g., pulse rate). In some example, the amplitude may be between approximately 0.1 volts and 50 volts, such as between approximately 0.5 volts and 20 volts, or between approximately 0.1 volt and 10 volts. In other embodiments, a current amplitude may be defined as the biological load in the voltage that is delivered. For example, the range of current amplitude may be between approximately 0.1 milliamps (mA) and 50 mA. In some examples, the frequency may be between about 0.5 Hz and about 500 Hz, such as between about 1 Hz and about 250 Hz, between about 1 Hz and about 20 Hz, or about 10 Hz.

As described herein, the stimulation parameters may define an electrical stimulation therapy with an intensity below a motor threshold of the target tissue being stimulation at a given pulse width and frequency. For example, the stimulation may have an intensity just below the motor threshold such that the stimulation does result in a motor evoked potential in the stimulated tissue but still inhibits contraction of at least one a bladder or bowel of the patient. The pulse width for the delivered electrical stimulation may be selected based on the chronaxie identified for patient 12, e.g., for a particular nerve site.

Memory 56 may include any volatile, non-volatile, magnetic, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processor 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 4:
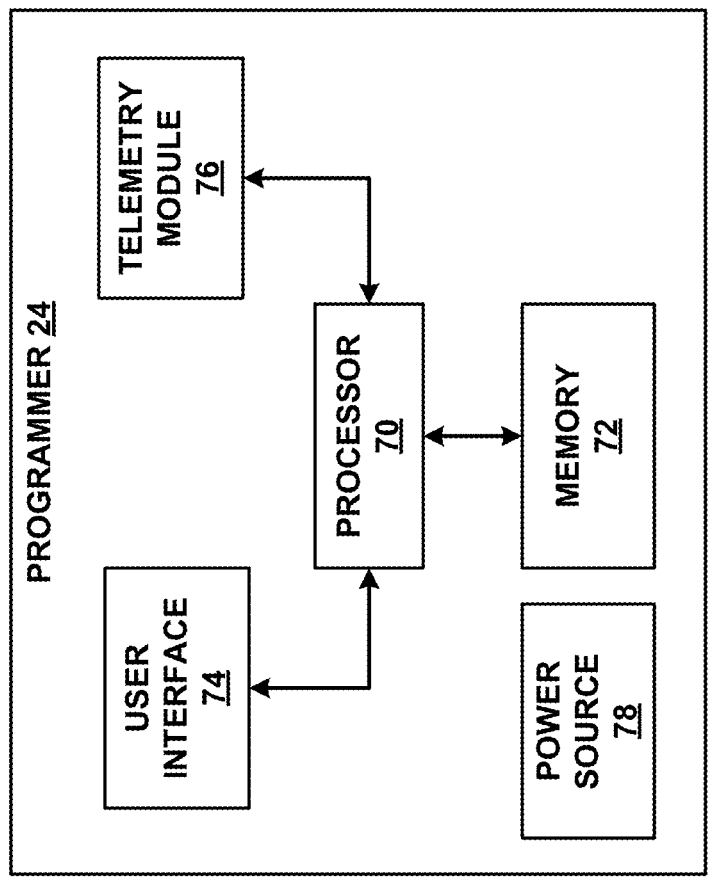
FIG. 4 is a functional block diagram illustrating an example configuration of the external programmer of the systems shown in FIGS. 1 and 2.

FIG. 4 is a functional block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a processor 70, memory 72, user interface 74, telemetry module 76, and power source 78. Memory 72 may store program instructions that, when executed by processor 70, cause processor 70 to provide the functionality ascribed to programmer 24 throughout this disclosure.

In some examples, memory 72 may further include therapy cycles defining stimulation therapy, similar to those stored in memory 56 of IMD 16. The therapy cycles stored in memory 72 may be downloaded into memory 56 of IMD 16. Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 70 can take the form one or more microprocessors, DSPs, ASICs, FPGAs, programmable logic circuitry, or the like, and the functions attributed to processor 70 herein may be embodied as hardware, firmware, software or any combination thereof.

User interface 74 may include a button or keypad, lights, a speaker for voice commands, and a display, such as a liquid crystal (LCD). In some examples the display may be a touch screen. As discussed in this disclosure, processor 70 may present and receive information relating to stimulation therapy via user interface 74. For example, processor 70 may receive patient input via user interface 74. The patient input may be entered, for example, by pressing a button on a keypad or selecting an icon from a touch screen. Patient input may include, but is not limited to, input that indicates an urge felt by the patient, a leakage incident experienced by the patient, an imminent voiding event predicted by the patient, or a voluntary voiding event to be undertaken by the patient.

Telemetry module 76 supports wireless communication between IMD 16 and external programmer 24 under the control of processor 70. Telemetry module 76 may also be configured to communicate with another computing device via wireless communication techniques, or direct communication through a wired connection. Telemetry module 76 may be substantially similar to telemetry module 58 described above, providing wireless communication via an RF or proximal inductive medium. In some examples, telemetry module 76 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer 24 without needing to establish a secure wireless connection.

In some cases, it may be desirable for IMD 16 to decrease the frequency of stimulation or even suspend the delivery of the stimulation configured to inhibit bladder contractions of patient 14 when patient 14 needs to void. In some examples, patient 14 may interact with programmer 24 (or directly with IMD 16 as described above) to control IMD 16 to withhold the stimulation that is intended to inhibit bladder contractions. Patient 14 may indicate an intent to void via user interface 74, and processor 70 may implement a blanking interval through communication of the indication to IMD 16 via telemetry module 76. For example, processor 70 may transmit a command signal to IMD 16 that indicates IMD 16 should temporarily suspend delivery of the stimulation therapy in response to command signal. In some cases, this may permit voluntary voiding by patient 14.

In other examples, IMD 16 may automatically determine when patient 14 is attempting to voluntary void, e.g., based on a voiding signature of an EMG signal indicative of bladder activity or based on bladder pressure or contraction. In such examples, IMD 16 may automatically suspend the delivery of electrical stimulation therapies to permit patient 14 to voluntary void. In some cases, suspension of stimulation by IMD 16 is not necessary to facilitate voiding, and stimulation may occur substantially simultaneously with the voluntary voiding. For example, the bladder volume will eventually increase to a level to trigger strong bladder contractions that prevails over the stimulation therapy to allow voiding.

Power source 78 delivers operating power to the components of programmer 24. Power source 78 may include a battery, for example a rechargeable battery. Recharging may be accomplished by using an alternating current (AC) outlet or through proximal inductive interaction between an external charger and an inductive charging coil within programmer 24.

Figure 5:
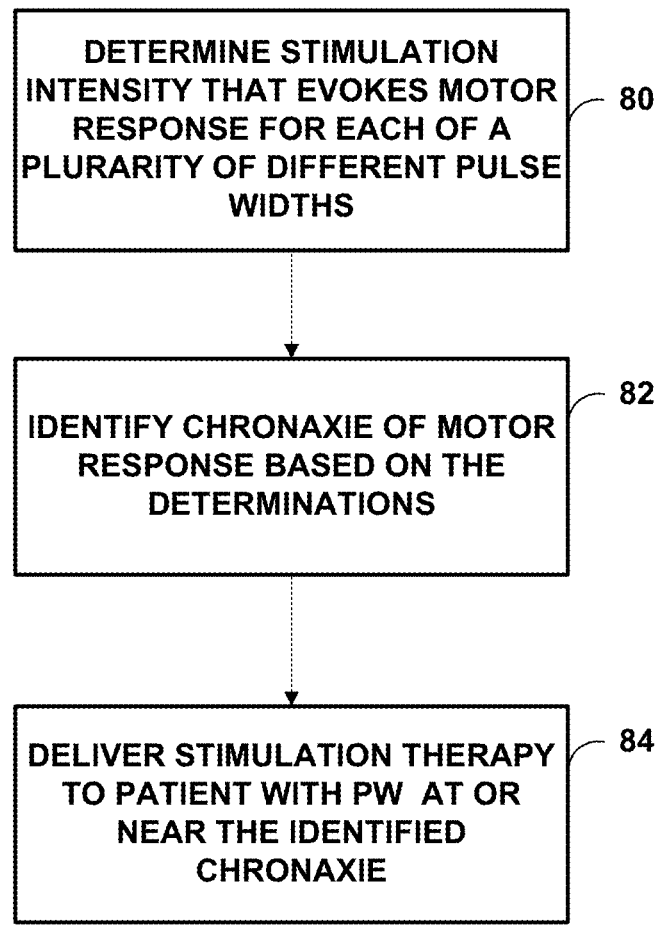
FIG. 5 is a flow diagram illustrating an example technique for delivering stimulation therapy to a patient to manage urinary incontinence.

FIG. 5 is a flow diagram of an example technique for delivering electrical stimulation to a sacral nerve of patient. For ease of description, the technique will be described as being performed by medical device system 10 of FIGS. 1-4. In some examples, the technique of FIG. 5 may be implemented as a set of instructions executable by processor 50 and stored by memory 56 of IMD 16 or a memory of another device. While processor 50 and memory 56 are primarily referred to throughout the description of FIG. 5, in other examples, a processor of another device (e.g., programmer 24) may perform any part of the techniques described herein, including the technique shown in FIG. 5, alone or in combination with another device. Although FIG. 5 is described with regard to system 10 of FIG. 1, other systems and devices employing the technique of FIG. 5 are contemplated.

In accordance with the example of FIG. 5, system 10 may identify the chronaxie for electrical stimulation delivered to the sacral nerve of patient 14 from IMD 16 that evokes a threshold motor response (82). Any suitable technique may be used to identify the chronaxie for electrical stimulation delivered to the sacral nerve of patient via IMD 16. In the example of FIG. 5, IMD 16, under the control of processor 50, may deliver electrical stimulation to the sacral nerve via one or more of electrodes 29 at plurality of different pulse widths while keeping the frequency constant (80). For each pulse width, the threshold intensity of the stimulation that evokes a motor response may be determined, e.g., by ramping/stepping up the amplitude of the stimulation from some nominal amount until a motor response is evoked by the stimulation (80). The evoked threshold motor response may be detected using any suitable technique including, e.g., based on a EMG signal and/or accelerometer signal sensed via sensor 22, local pulsation, patient feedback indicating sensation of a motor response or other sensation such as tingle, which may occur earlier than an evoked motor response, and the like. Patient feedback may be input by patient 14 or clinician via programmer 24. For example, patient 14 may provide input indication a sensation corresponding to activation of nerve fibers as a result of electrical stimulation at a set pulse width while the amplitude of the stimulation is ramped/stepped up. Such a process may be repeated at a plurality of difference pulse width (e.g., as a fixed frequency) to identify the chronaxie for the electrical stimulation delivered to the sacral nerve of patient 14.

Processor 50 and/or 70 may then determine the chronaxie for the electrical stimulation delivered to the sacral nerve based on the determined thresholds for each of the pulse widths. In one example, processor 50 may identify the rheobase for the delivered electrical stimulation, and then determine the pulse width at which an amplitude twice the rheobase evoked at threshold evoked motor response. In some examples, the described "test" stimulation therapy at a plurality of different pulse widths may be used to generate a plot similar to the strength-duration plot show in FIG. 6, and the chronaxie of the stimulation may be determined using the generated plot. For example, using a set of data points identifying a response thresholds for various pulse widths, the chronaxie and rheobase may be calculated with a non-linear fit to $Y=(Y_0-N_S)*\exp^{(-K*X)}+N_S$, where Y is the EMG response (assessed either visually or via the EAS electrodes), X is the pulse width, $Y_0$ is the initial value, $N_S$ is the rheobase, and K is the inverse of the chronaxie. However, other techniques may be utilized to determine the chronaxie in a manner that is specific to patient 14, e.g., rather than estimating the chronaxie based on deliver of similar stimulation to one or more other patients.

IMD 16 may then be programmed using programmer 24 to deliver electrical stimulation to the sacral nerve of patient 14 with a pulse width at or near the identified chronaxie (84) to treat incontinence or other disorder of patient 14. For example, the pulse width may be within about 50%, about 40%, about 30%, about 20%, about 10%, about 5%, or about 1% of the identified chronaxie. As another example, the pulse with may be within at least one of about 50 microseconds, about 40 microseconds, about 30 microseconds, about 20 microseconds, about 10 microseconds, about 5 microseconds, or about 1 microsecond of the identified chronaxie. The frequency (e.g., pulse rate) of the sacral nerve stimulation may be the same or substantially similar to the frequency of the "test" stimulation to identify the chronaxie. The amplitude of the sacral nerve stimulation may be just below the threshold that evokes a motor response at the defined pulse width and frequency. In this manner, the sacral nerve stimulation may inhibit the contraction of the bladder and/or bowel of patient 14 without evoking a motor response.

The technique of FIG. 5 may be performed during a programming session (e.g., an initial programming session after the implantation of IMD 16) and/or periodically throughout the chronic delivery of sacral nerve stimulation to treat patient 16 to re-determine the chronaxie of the stimulation, which may change over time. For example, the re-determination may occur periodically based on a predetermined schedule and/or based on patient input (e.g., when patient 16 believes that the sacral nerve stimulation therapy is no longer effectively treating the patient condition).

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise RAM (e.g., synchronous dynamic random access memory (SDRAM)), ROM, NVRAM, EEPROM, FLASH memory, magnetic or optical data storage media, and the like.

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

EXPERIMENTAL RESULTS

Multiple studies were carried out to evaluate one or more aspects of example of the disclosure. Those studies are described below. However, the disclosure is not limited by the studies or the corresponding description.

Study One—Motor Responses to S3 Sacral Nerve Stimulation in Sheep

One object of the first sheep study was to characterize the strength-duration (SD) response of external anal sphincter (EAS) activation as assessed both visually and with EMG in response to the third sacral foramen (S3) sacral neuromodulation (SNM). SNM at the S3 is an FDA-approved therapy for urinary urge incontinence, urgency-frequency and fecal incontinence. In some examples, a recommended pulse width for SNM is 210 µs, but the SD response from S3 SNM has not been fully elucidated. A positive motor response in the EAS can be a candidate predictor for clinical efficacy.

Methods:

Four adult female Polypay sheep were used for this study. The age of the sheep ranged from 18 to 39 months (mean: 31 months) with weights ranging from ranging from 64 to 92 kilograms (kg) (mean: 78 kg). A pair of sensing electrodes, with inter-electrode distance of about 1 cm were implanted in the EAS at the three and nine o'clock positions. The lead bodies were tunneled cranially and exteriorized. A two cm skin incision was made in the perineum lateral to the tail, and subcutaneous tissue was dissected until the EAS was palpated. Two foramen needle introducers were passed from just lateral to the vulva dorsally, through the EAS, and out the subcutaneous tissue dissection plane. The sensing electrodes (Medtronic Model 431, 35 cm length, Medtronic Inc., Minneapolis, Minn., USA) were passed into each introducer. The introducers were removed and the electrodes were sutured into the EAS.

Tined, quadripolar electrode leads (Medtronic Model 3889) were implanted bilaterally in the S3 foramina. The lead bodies were tunneled cranially and exteriorized. Concurrent electrical stimulation during lead placement was used to assess the best placement. The final lead placement was chosen based on lowest stimulation threshold seen in the EAS.

Variable intensity (0.1V to 10V), 10 Hz stimulation was delivered unilaterally to electrodes 3(−) & 0(+) for 10 to 300 µs pulse widths. Balanced, biphasic stimulation was delivered with a Biopac STM100C (Biopac Systems, Inc., Goleta, Calif., USA). A 100 us inter-phase interval was present between the cathodic and anodic phases. In two sheep, the SD curves were assessed independently from both pairs of S3 leads. In another sheep, two sets of SD curves were collected from the same lead on different days.

EMG was collected from the two bipolar pairs in the EAS to assess EAS contraction. Biopac EMG100C sense amplifiers were used. The HP pole was 10 Hz, the LP pole was 5 kHz, gain was 2000, and the sampling rate was 25 kHz. EAS contraction was also assessed visually.

Results and Discussion

SD response thresholds were plotted against the cathodic pulse width. The chronaxie and rheobase were calculated with a non-linear fit to $Y=(Y_0-N_S)*\exp^{(-K*X)}+N_S$, where Y is the EMG response (assessed either visually or via the EAS electrodes), X is the pulse width, $Y_0$ is the initial value, $N_S$ is the rheobase, and K is the inverse of the chronaxie. All data was expressed as mean±standard error of mean. The EMG area-under-the curve (AUC) for three different pulse widths (10 µs, 60 µs and 210 µs) was also plotted as a function of stimulation amplitude.

Figure 8A:
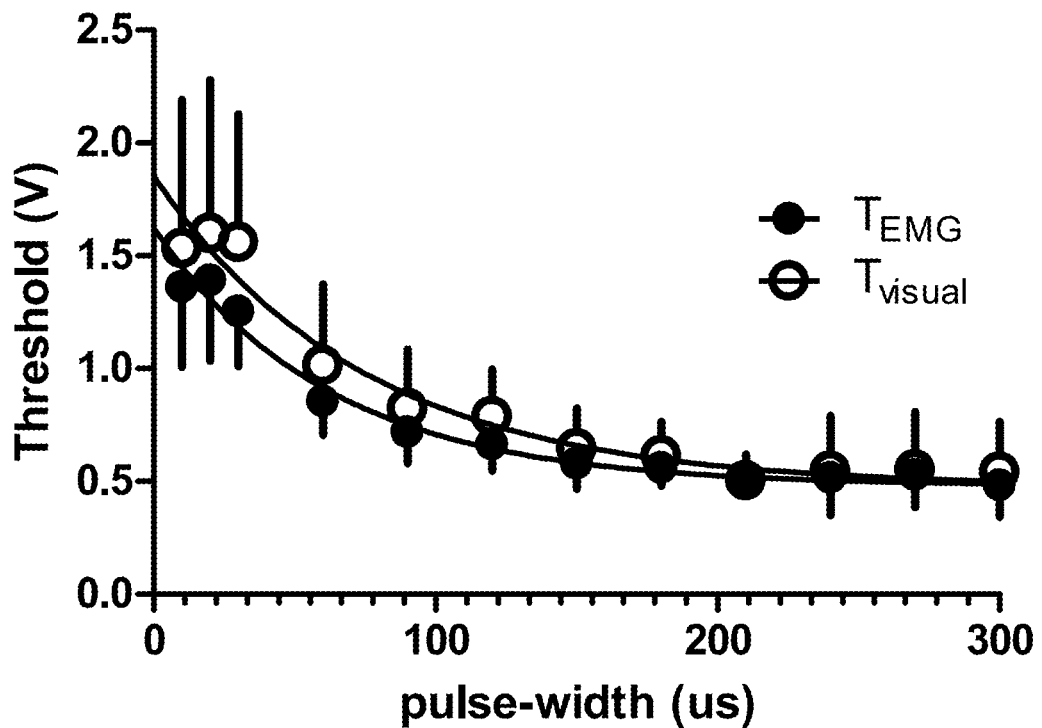
Figure 8B:
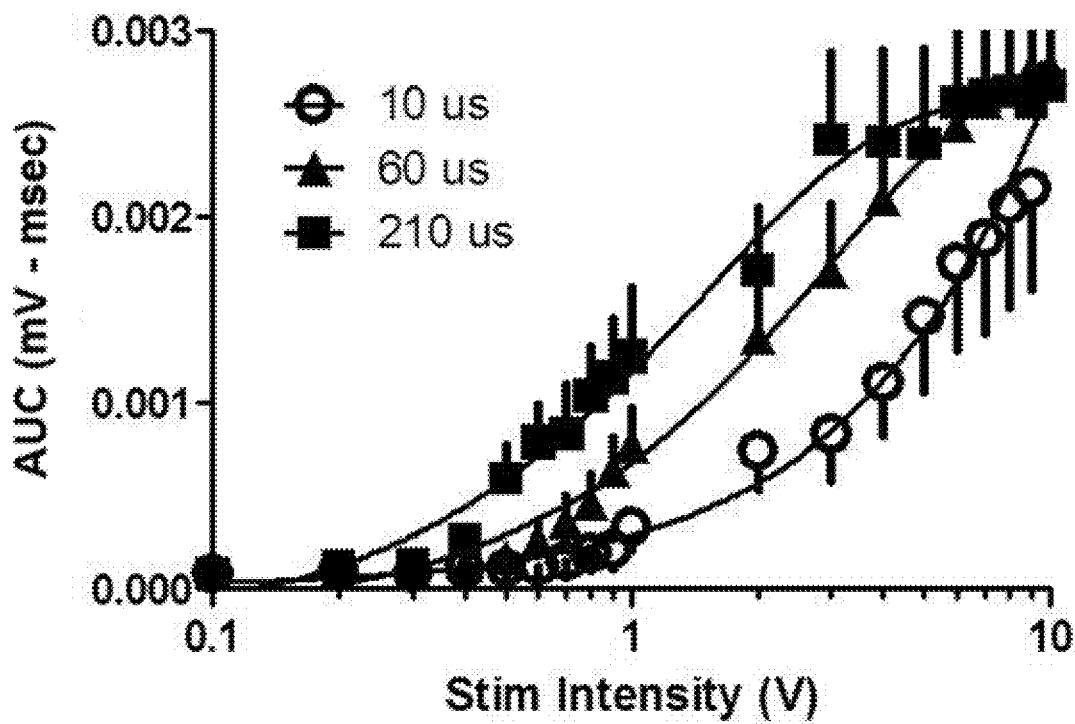

FIG. 8A is the plot of SD curves for both the EMG and visually assessed EAS contraction threshold. The chronaxie and rheobase for the EMG assessed SD curves was 62.03±0.001 us and 0.48±0.29V. The chronaxie and rheobase for the visually assessed SD curves was 74.35±0.001 µs and 0.48±0.12V, respectively. The amplitude required to evoke an EAS contraction with 10 µs cathodic pulses as assessed both with EMG and visually was 1.62±0.22V and 1.85±0.39V respectfully. FIG. 8B is the plot of EMG area-under-the curve (AUC) for three different pulse widths (10 µs, 60 µs and 210 µs) as a function of stimulation amplitude.

Based on the results, the chronaxie for EAS activation in response to S3 SNM in normal physiology sheep was determined to be significantly lower than the standard 210 µs pulse width used clinically. It was unknown if SNM at shorter pulse widths has equivalent clinical efficacy to that at 210 µs.

Study Two—Sacral Neuromodulation in Sheep

One object of the second sheep study was to characterize the EMG responses of the EAS to different pulse widths (PWs) of S3 SNM in anesthetized and awake sheep. Quadripolar tined leads were implanted adjacent to the S3 nerve root bilaterally to deliver SNM and two pairs of intramuscular leads were placed on either side of the EAS for EMG sensing. The EMG responses to SNM with different PWs (ranging from 0.03 milliseconds (ms) to 0.3 ms) were examined using variable intensities from 0.1 V to 5 V.

Methods:

Fourteen S3 nerve roots from seven adult, female Polypay sheep (two roots per sheep) were used for the study. The animals ranged in age from 18 to 39 months (mean: 31 months) and weight from 64 to 92 kg (mean: 78 kg) at time of implant. The sheep were prepped with intramuscular morphine (0.5 mg/kg), induced with intravenous propofol, and maintained on isoflurane. To deliver S3 neuromodulation, Medtronic Model 3889 tined quadripolar leads (28 cm length) were inserted through the left and right side of the sacral foramen, respectively. The S3 foramina were identified under fluoroscopic guidance and electrical stimulation was used to verify appropriate motor responses of perianal, tail, or bellows contractions with minimal leg contractions. The final lead placement was chosen based on the stimulation threshold for motor response at the designated location with the lowest stimulation voltage. The leads were tunneled to separate sub-dermal pockets cranially and anchored at the externalization site.

Figure 7:
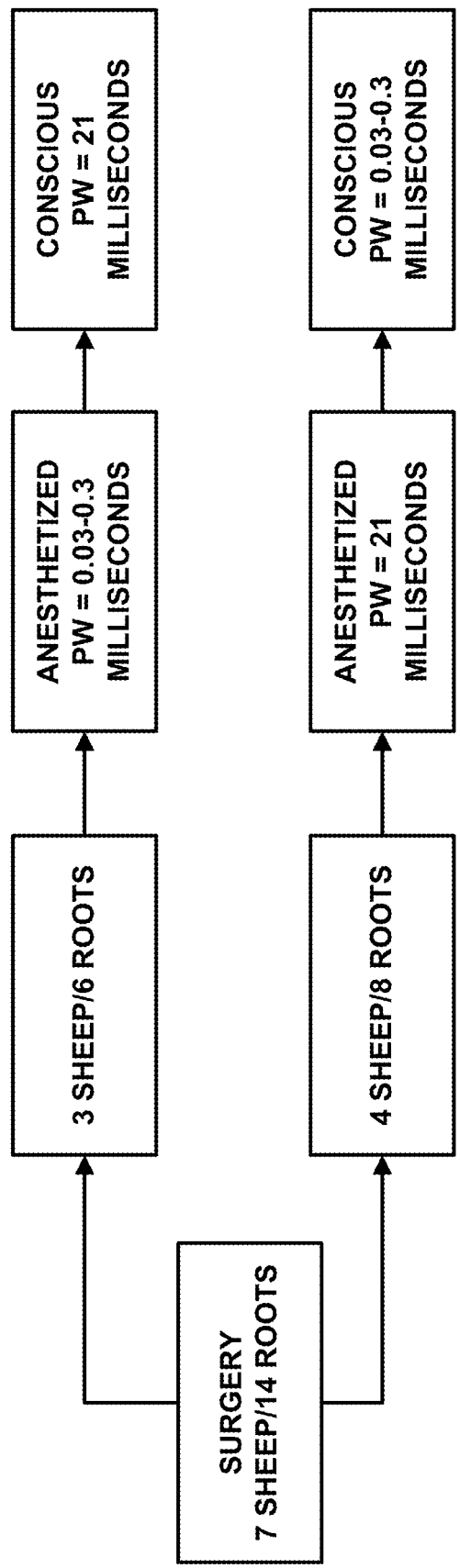
FIGS. 7 to 11B relate to first and second sheep studies that are described further below.

FIG. 7 is a flowchart summarizing a trial schedule for the sheep study. In all seven sheep, EMG responses were recorded initially under anesthesia of propofol and isoflurane, and a couple of weeks later in an awake condition. Sacral nerve stimulation was delivered with a stimulator, which was connected to the externally tunneled quadripular lead. The stimulator parameters were bipolar 10 Hz, and electrodes 3 and 0 as the cathode and anode, respectively. Pulse widths and stimulation amplitudes were swept through various values to develop threshold-PW curves.

Response thresholds were obtained from both visual detection (Tvisuai) and EMG waveform analysis against the stimulus intensity. Tvisuai was determined by the stimulation intensity which triggered the first visible appearance of a motor response to ascending intensity of consecutive 10 Hz stimuli and further confirmed by disappearance of motor response to decreasing stimulation intensity. The evaluated parameters of EMG response include threshold (TEMG) and the area under the curve (AUC, represented by mV-msec) of integrated and calculated EMG action potentials. Responses to stimulation on each nerve root were plotted against the voltage intensity on a semilogarithmic scale. The TEMG of each individual response was defined as the intensity at which evoked potentials were distinguished from basal activity in the EMG detection window and increased to at least three ascending intensities of consecutive 10 Hz stimuli.

To assess the effect of PW on motor function, $T_{visual}$s or $T_{EMG5}$ were plotted against PW. The chronaxie and rheobase were calculated according to the equation $Y=(Y_0-N_S)*\exp^{(-K*X)}+N_S$, where Y is threshold response, X is the pulse width, and $Y_0$ is the threshold value when the pulse width is close to zero. $N_S$ is the rheobase (the intensity needed for excitation with a very long or infinite pulse). K is the rate constant in inverse units of pulse width. The half-life (chronaxie) equals the ln(2) divided by K. The value of threshold charge (voltage*PW) to different PWs were compared using analysis of variance (ANOVA).

Results and Discussion

The EMG responses from ipsilateral EAS (kAs) and contralateral EAS (CEAs) were compared. The EMG responses from kAs appeared significantly stronger than that from CEAS. The late component EMGs from the CEAs tended to be more sensitive to a lower intensity of nerve stimulation in awake sheep. The strength-duration responses from the IEAs as ascertained visually and with EMG in anesthetized and awake sheep were fitted with a monoexponential nonlinear regression. The resulting time constants (chronaxie) were of 0.05 ms (n=6), and 0.04 ms (n=6) and 0.04 ms (n=8), respectively.

Figure 9A:
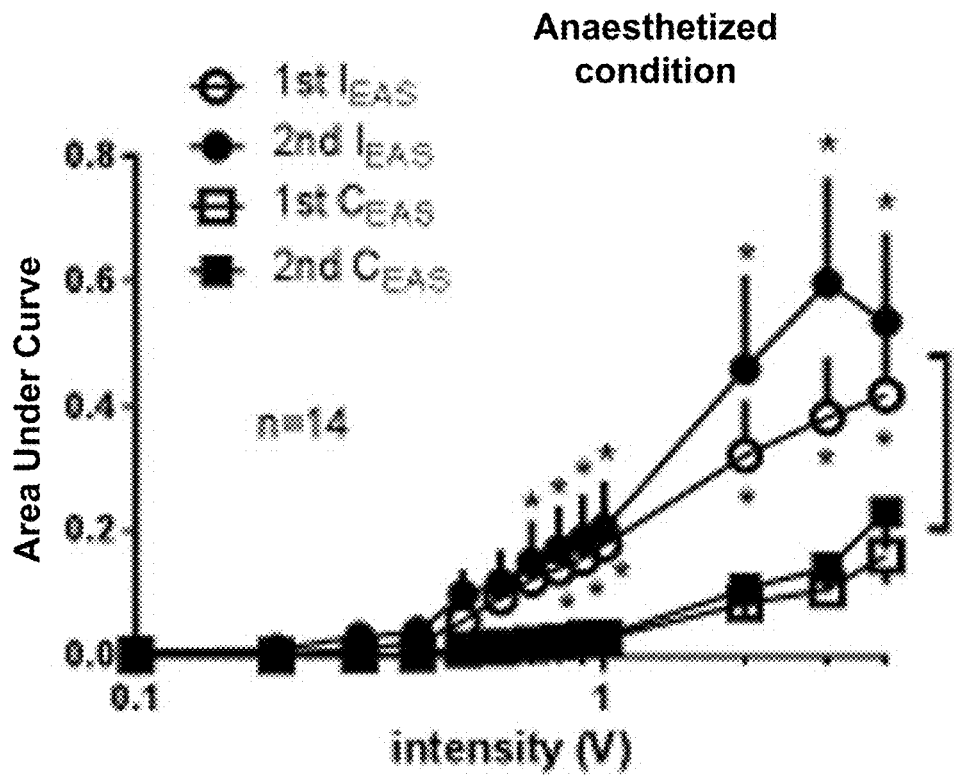
Figure 9B:
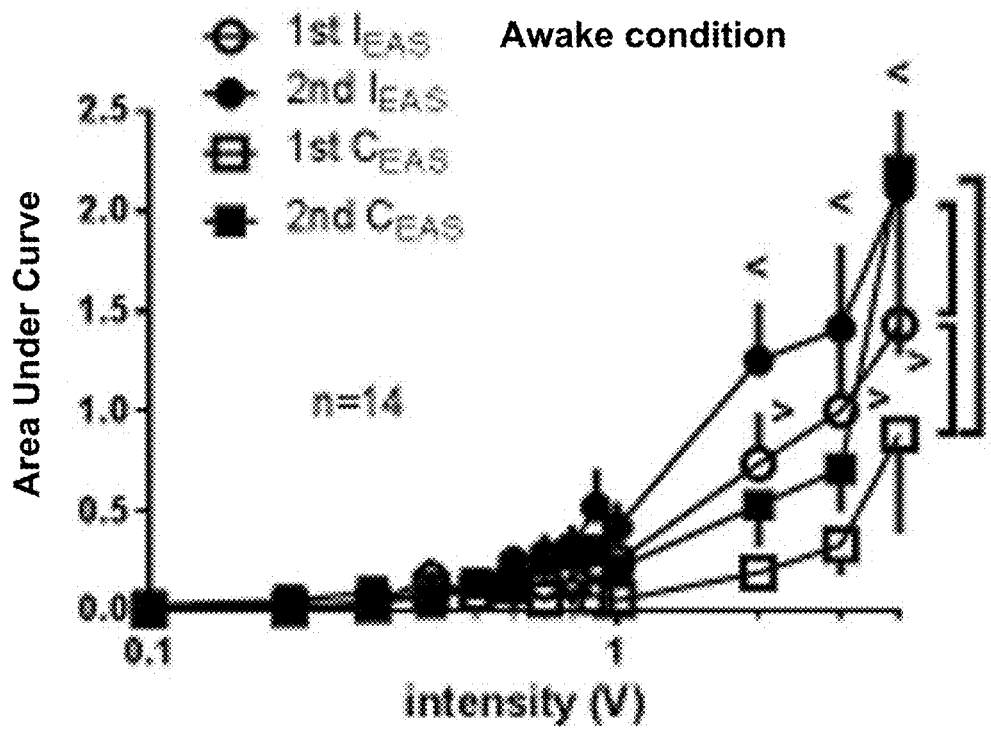

FIGS. 9A and 9B are plots summarizing the stimulus-response functions of two components of EMG activities from kAs and CEAS to graded intensities of the SNM (i.e., intensity-response) in anaesthetized (FIG. 9A) and awake conditions (FIG. 9B). The EMG responses were larger in amplitude as the stimulation intensity was increased. The kAs EMGs appeared significantly stronger than CEAs in anesthetized condition (p<0.05, two-way ANOVA, Bonferroni post-test, FIG. 9A). In the conscious condition, the IEAs EMGs remained significantly stronger than CEAS EMGs. In addition, the second component of CEAS EMG occurred sensitive to SNM, with a higher response amplitude.

Figure 10A:
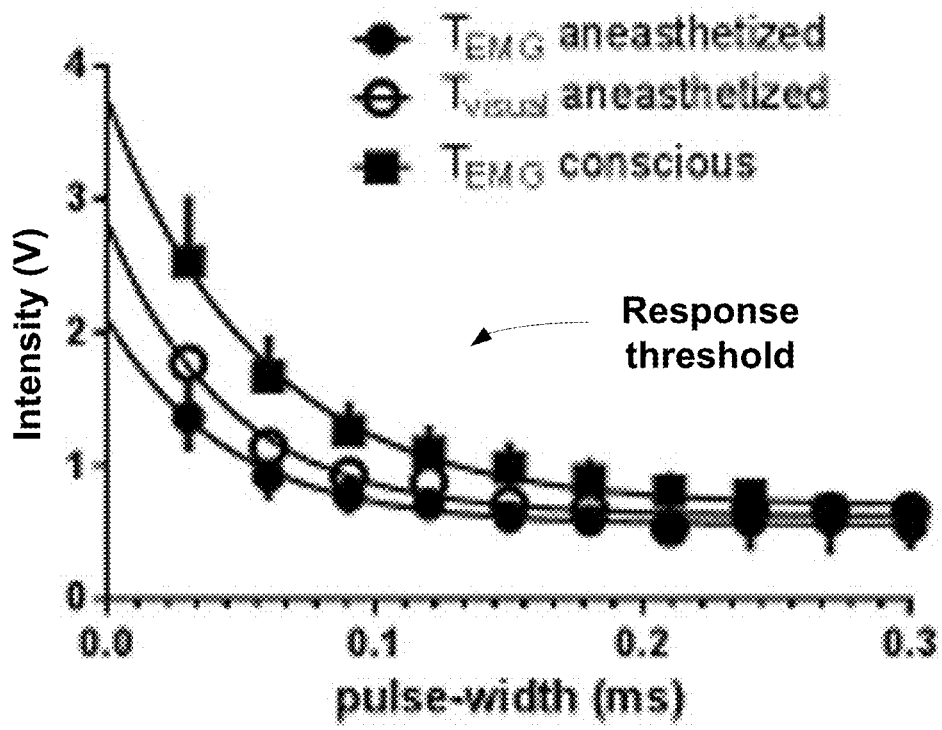

FIG. 10A is a plot summarizing the response thresholds from either visual detection ($T_{visual}$) or EMG waveform analysis from the ipsilateral EAS (TEMG) against the stimulus PW to demonstrate the minimal stimulation required to activate the S3 nerve at a given PW in anaesthetized and conscious conditions. The solid curves are monoexponential nonlinear regression fits and gives time constants of 0.05 ms (95% CI: 0.03-0.08, n=6), and 0.04 ms (95% CI: 0.03-0.06, n=6) and 0.04 ms (95% CI: 0.02-0.11, n=8), respectively. The rheobase values were 0.39±0.05 V, 0.42±0.03 V, and 0.70±0.14 V, respectively. The maximal values to minimal PW were 1.53±0.16 V, 1.57±0.11 V and 3.74±0.70 V, respectively.

Figure 10B:
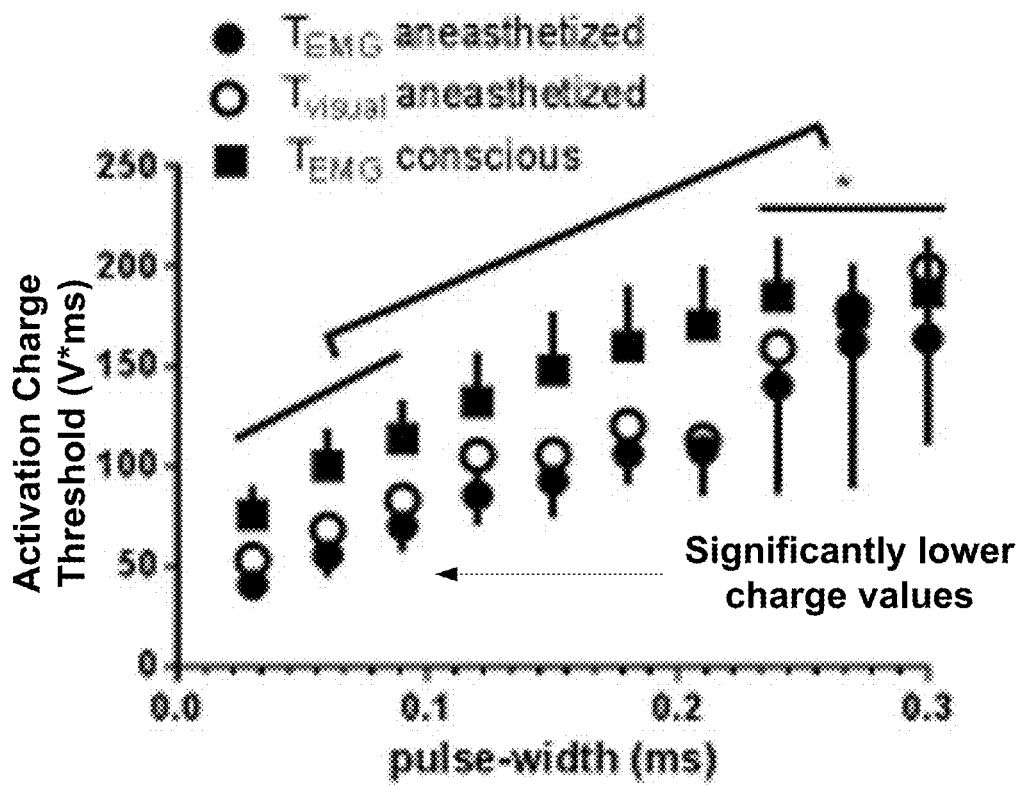

FIG. 10B summarized the activation charge threshold (mV*ms) to different PW stimulation. One-way ANOVA demonstrated significantly lower charge values (more efficient) to shorter PWs of 0.03 ms, 0.06 ms or 0.09 ms in comparison to longer (≥0.24 ms) PWs (p<0.05, Bonferroni post-test's post test).

Figure 11A:
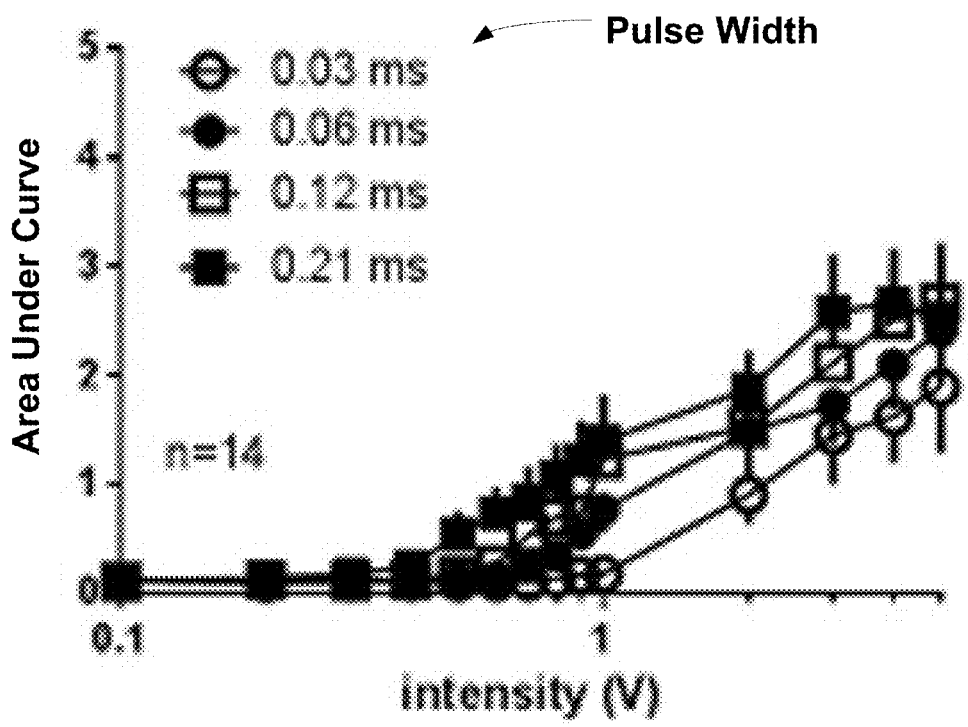
Figure 11B:
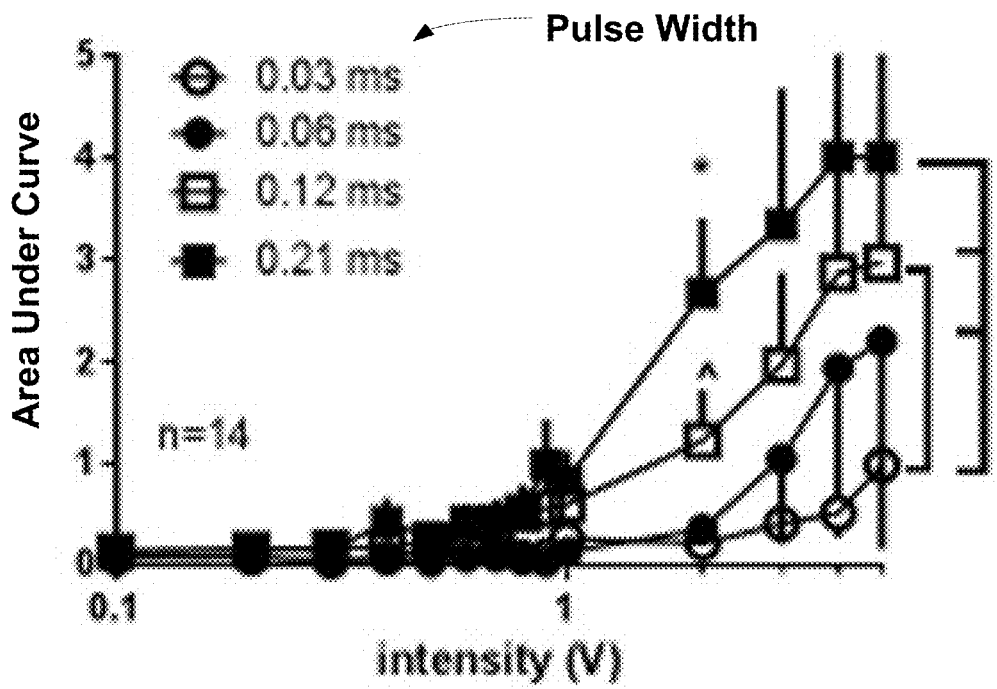

FIGS. 11A and 11B are plots summarizing the stimulus-response function of increased EMG activities from the EAS when the PWs were 0.03 ms, 0.06 mn, 0.12 ms and 0.21 ms in anesthetized (FIG. 11A) and awake conditions (FIG. 11B). EMG response was stronger as the stimulation intensity increased. This effect is significantly greater to longer PW stimulations (FIG. 11B, e.g. 0.21, 0.12 ms) than that produced by short PW stimulation (e.g. 0.03 ms, p<0.05, repeated measures ANOVA).

In the second sheep study, clinical sacral neuromodulation therapy was mimicked via SNM leads insertion through the S3 sacral foramen. The evoked EMG responses of the EAS, a physiomarker of sacral neuromodulation, was measured for different pulse width S3 SNM. The study results demonstrated a 0.04-0.05 ms chronaxie for this locus of neurostimulation. Accordingly, it was determined that shorter pulse width SNM may be advantageous owing to minimized energy consumption from the implantable neurostimulator battery, versus the 0.21 ms pulse which is generally used as the clinical standard. Reducing pulse width would be expected to significantly increase the window between battery replacements. Potential battery savings manifested by shorter pulse width would provide more efficient therapy delivery and increased longevity of the stimulator.

Based on response threshold and pulse width response curves, short pulse widths correlate significantly to lower charge values in comparison to longer pulse widths. Setting the stimulation intensity close to the chronaxie may allow that shorter pulse widths reduce the stimulation charge. Pulse width also affects the relative selectivity of stimulation among different types of nerve fibers (diameter). Shorter pulse widths will increase the differences in motor thresholds from different diameters of nerve fibers. The threshold difference between large and small nerve fibers increases along with the increase in the relative distance between the stimulating electrode and the nerve fibers. Thus, preferential activation of large nerve fibers over small fibers can be more pronounced with a shorter pulse width stimulation. Therefore, shorter pulse width stimulation may reduce discomfort due to higher nerve fiber selectivity compared to the 0.21 ms PW that is widely used clinically.

Study Three—Spinal Nerve Stimulation of Rats

One object of the rat study was to investigate the spinal nerve stimulation (SNS) evoked motor threshold ($T_{mot}$) response across different PWs, and assess a subset of selected stimulation PWs with respect to bladder reflex contraction (BRC). The study described the motor threshold ($T_{mot}$) responses-PW of SNS at a range of 0.02 ms to 0.3 ms. When the chronaxie of the $T_{mot}$-PW curve was identified, a subset of PWs (0.03 ms to 0.21 ms) was tested at the frequency of 10 Hz and individual $T_{mot}$ intensity on the micturition reflex in a rat model of isovolumetric bladder contraction.

Methods:

Wire electrodes were placed under each of the L6 spinal nerves in anesthetized female Sprague-Dawley rats to produce bilateral SNS. The rats weighed 200 grams (g) to 300 g (n=46) and were anesthetized with urethane (two i.p. injections, 4 min apart, total 1.2 g/kg). The anesthetized rats were maintained at 37 degrees Celsius with a heating pad during the studies and were euthanized by $CO_2$ asphyxia upon completion of experimental procedures.

To deliver electrical stimulation, a wire electrode was placed on each side of the L6 spinal nerve. The L6/S1 posterior processes were exposed after a dorsal midline incision was made from approximately L3 to S2. The S1 processes were removed and the L6 nerve trunks localized caudal and medial to the sacroiliac junction. A wire electrode was placed with bared segments of teflon-coated, 40-guage, stainless steel wire under each nerve. Silicone adhesive was then applied to cover the wire around the nerve, and the skin incision was sutured shut. The electrode was connected to a Grass S88 stimulator, through a stimulus isolation unit (SIU-BI, Grass Medical Instruments), and needle electrodes under the skin of the tail served as the ground.

SNS evoked hind-toe twitches and/or pelvic floor muscle contraction. The motor response threshold current ($T_{mot}$) was evaluated across the PW range from 0.02 ms to 0.3 ms of biphasic pulses (10 Hz) in 11 rats. $T_{mot}$ was defined as the lowest intensity to evoke the first, barely discernible, skeletal muscle contraction. It was determined as the stimulation intensity which triggered the first visible appearance of motor response to ascending intensity of consecutive 10 Hz stimuli and further confirmed by disappearance of motor response to decreasing stimulation intensity. This procedure was then repeated two more times for added confirmation.

In each of the 35 rats in which bladder contraction was recorded, a cannula (size PE50) was placed into the bladder via the urethra, and secured with a suture tie. The urethral cannula was connected via a T-type connector to a pressure transducer of the data acquisition system (ADInstrument MLT0380D, Colorado Springs, Colo., USA) and the intravesical pressure signal was put through a DC amplifier (ADInstrument, ML119). The other end of the T-type connector was attached to a syringe pump. To induce BRC, saline was infused into the bladder via the syringe pump at a rate of 0.05 mL per minute to induce a micturition reflex (defined as bladder contraction of a magnitude >10 mmHg in the study). The infusion rate was then lowered to 0.01 mL per minute and continued until 3 to 5 consecutive contractions were established. After initiating perpetual BRC in this manner, saline infusion was terminated.

After a 15-min control period, nerve stimulation was applied for 10 minutes. The $T_{mot}$ was first determined by 0.1 ms PW stimulation and further adjusted and confirmed by disappearance or/and re-appearance of motor response to the tested PW ranging from 0.03 ms to 0.21 ms. The $T_{mot}$ was measured on each root side separately, to allow for potential differences between left and right nerve roots. Stimulation intensities at a given PW were then maintained for 10 mins. The BRC was recorded for 20 minutes post stimulation. Each trial of recording lasted for 45 minutes including a 15 minutes control, 10 min nerve stimulation, and 20 min post-stimulation. Two trials of the testing were performed with a random stimulation parameter in 29 rats. The bladder was emptied after finishing the first trial and BRC was re-established by saline infusion. The second stimulation was applied at least 40 min after the first stimulation. A total of 64 trials were studied in 35 rats.

Results and Discussion

The $T_{mot}$ response was plotted against PW using a monoexponential nonlinear regression to elucidate the effect of PW on motor function. The chronaxie and rheobase were calculated according to the equation $Y=(Y_0-N_S)*\exp^{(-K*X)}+NS$, where Y is $T_{mot}$ response, X is PW, and $Y_0$ is $T_{mot}$ value when PW is close to 0. NS is the rheobase (that is, the intensity needed for excitation with a very long or infinite pulse). K is the rate constant in inverse units of PW. The half-life (chronaxie) equals the ln(2) divided by K. The value of $T_{mot}$ current charge (current*PW) to different PWs were compared using analysis of variance (ANOVA). Tukey's multiple comparison post test was used to determine the statistical significance between individual PW points.

For effect of PW on BRC, the frequency of BRC were calculated in 5 minute bins, having three control periods, two periods during stimulation, and four periods after stimulation. SNS does not reduce the amplitude of bladder contractions, therefore only effects on frequency/interval of BRC were studied. All data were compared to the mean response during the last 5 minutes prior to stimulation. Mean values of 10-min before, during and post stimulation were analyzed with Student's paired t-test (Prism 5 GraphPad Software Inc., San Diego, Calif.). The amplitude changes of inhibitory effects caused by 10 minute SNS to different PWs were compared using a repeated measures analysis of variance (ANOVA) with multiple comparisons (Prism 5 GraphPad Software). All data us expressed as mean±SEM and a value of $p<0.05$ was considered statistically significant.

SNS evoked muscle contraction observed visually and the muscle contraction became stronger. Additional muscle groups at more locations were involved as the stimulation intensity was increased. It was observed that there was no difference in motor responses between SNS on the left and right nerve roots (n=11, p>0.05, Two-way ANOVA). The $T_{mot}$ currents at which first visible motor contraction occurred with 0.03 ms PW stimulation on the left and on the right were 0.39±0.12 mA and 0.53±0.14 mA, respectively.

Figure 12B:
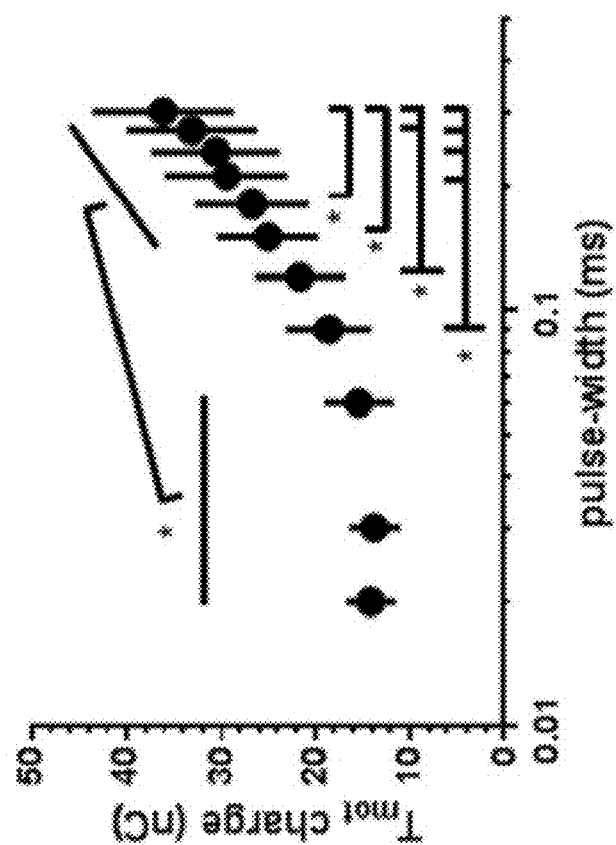
Figure 12A:
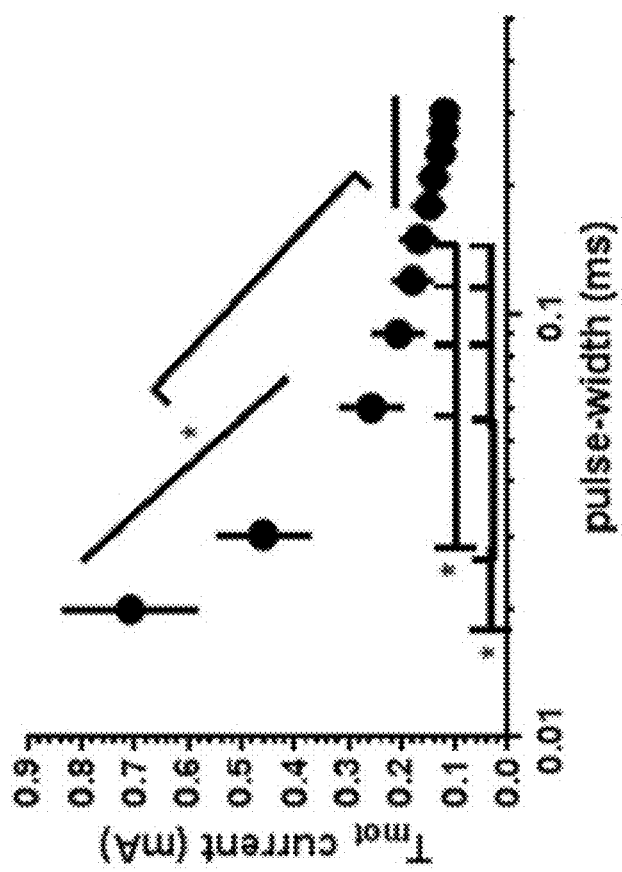

FIGS. 12A and 12B summarize data of visual motor threshold responses to graded pulse-width of bilateral spinal nerve stimulation (n=22, two nerve roots in 11 rats). FIG. 12A is a plot summarizing visual $T_{mot}$ current intensities against corresponding stimulation PWs. As shown in the plot of FIG. 12A, the motor thresholds current values lower as the pulse widths are increased. The monoexponential nonlinear regression analysis gives chronaxie of 0.04±0.002 ms. The rheobase values were 0.12±0.02 mA. The maximal values to minimal pulse-width were 0.71±0.13 mA. The motor thresholds to shorter PW stimulation of 0.02 ms, 0.03 ms or 0.06 ms were significantly higher in comparison to longer (≥0.18 ms) PWs (0.02 ms vs PW≥0.03 ms, p<0.002; 0.03 ms vs PW≥0.06 ms, p<0.002; 0.06 ms vs PW≥0.18 ms, p=0.033, Tukey's post test).

FIG. 12B is a plot summarizing the activation charge threshold ($T_{mot}$, nC) versus different PW stimulation. One-way ANOVA demonstrated significantly lower charge values (which may be more efficient) to shorter PWs of 0.02 ms, 0.03 ms or 0.06 ms in comparison to longer (>0.15 ms) PWs (0.02 ms or 0.03 ms vs PW>0.15 ms, p<0.002; 0.06 ms vs 0.15 ms, p=0.033; 0.06 ms vs PW≥0.18 ms, p<0.002, Tukey's post test). Statistical differences were also obtained for comparisons between other pairs, 0.09 ms vs PW≥0.21 ms (p<0.002), 0.12 ms vs PW≥0.27 ms (p<0.002), 0.15 ms vs 0.3 ms (p=0.002), and 0.18 ms vs 0.3 ms (p=0.033).

FIGS. 13A and 13B are plots of experimental records showing no significant change in isovolumetric bladder contraction (mmHg) without electrical stimulation (FIG. 13A), and abolished bladder contractions to 0.06 ms pulse-width (PW), motor threshold intensity, 10 Hz of bilateral spinal nerve stimulation (FIG. 13B).

Figure 14A:
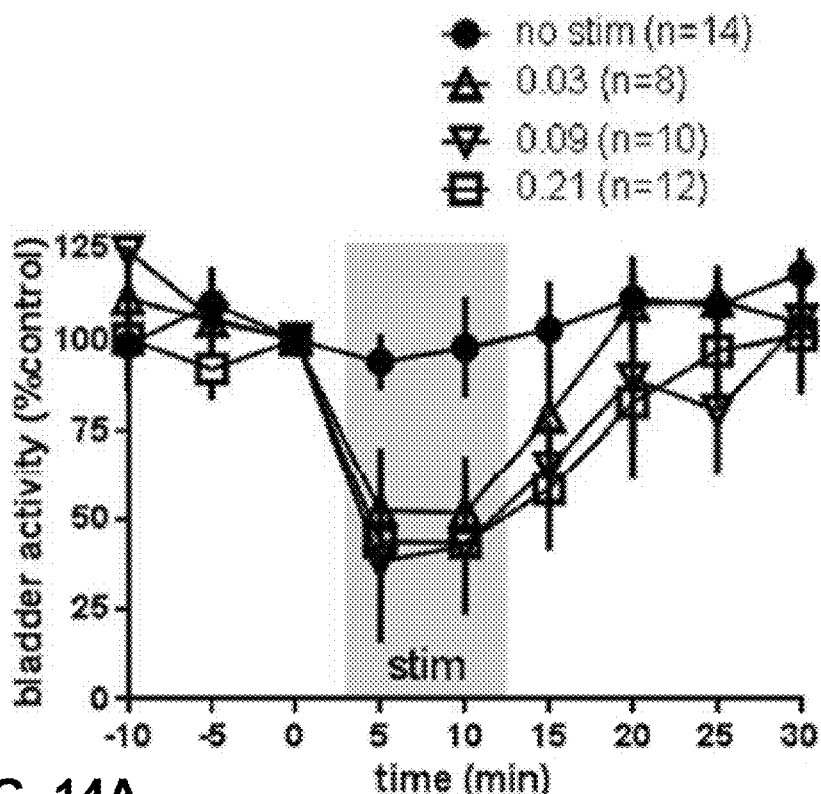
Figure 14B:
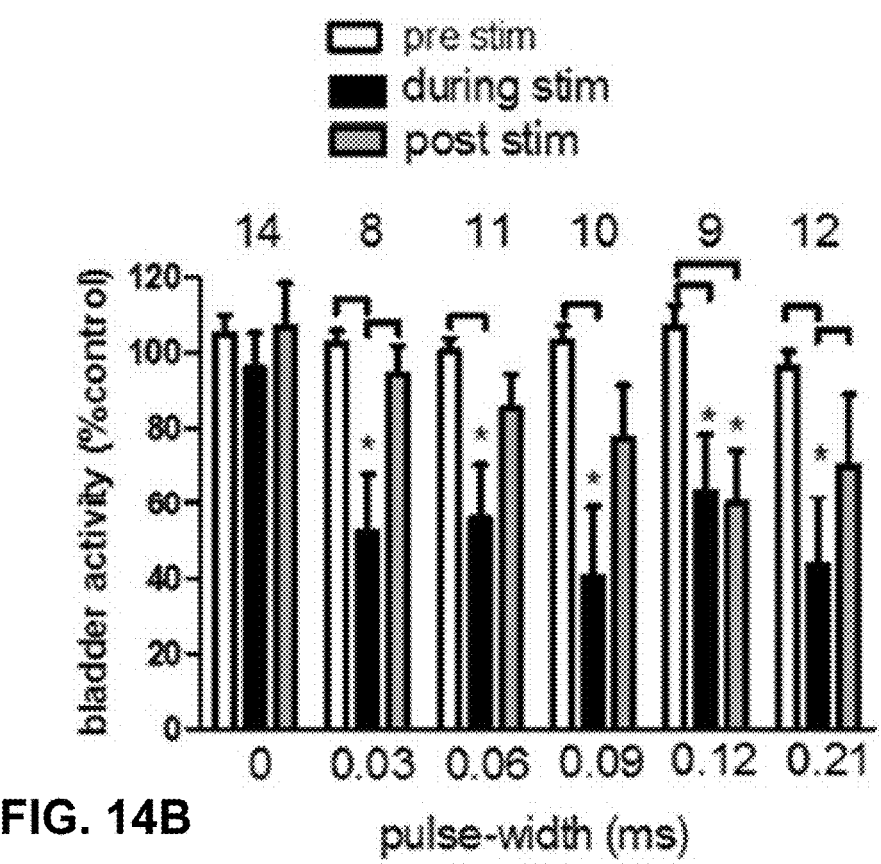

FIGS. 14A and 14B are plots illustrating the effects of spinal nerve stimulation at different pulse-widths (motor threshold, 10 Hz) on the frequency of the bladder reflex contraction. In FIGS. 14A and 14B, the responses are represented as a percentage of control (% control), where the baseline response before stimulation is defined as 100%.

FIG. 14A plots the time course of the mean responses of BRC frequency without SNS or with SNS at PWs of 0.03 ms, 0.09 ms and 0.21 ms. Maximal inhibition appeared during stimulation. After termination of the stimulus, bladder contractions returned to control levels.

FIG. 14B summarizes stimulation PW effects on BRC in 10-min periods before (pre-stim), during stim, and after SNS (post-stim). Among tested PWs of 0.03 ms (n=8; $T_{mot}$: 0.11±0.02 mA or 3.27±0.70 nC), 0.06 ms (n=11; 0.12±0.02 mA or 6±1.31 nC), 0.09 ms (n=10; 0.19±0.03 mA or 16.88±2.64 nC), 0.12 ms (n=9; 0.12±0.03 mA or 14.9±4.14 nC), and 0.21 ms (n=12; 0.16±0.03 mA or 34.34±5.90 nC), all produced statistically significant inhibition on bladder contractions. Maximal inhibition appeared during stimulation, while after termination of the stimulus, bladder contractions returned to control levels in about 10 mins. SNS at 0.03 ms, 0.06 ms, 0.09 ms, 0.12 ms and 0.21 ms decreased bladder contraction frequencies from 103±3%, 100±4%, 103±4%, 107±6% and 96±4% of controls, respectively, to 52±16% (n=8, p=0.02, paired t test), 56±15% (n=11, p=0.02), 40±19% (n=10, p=0.01), 64±15% (n=9, p=0.03), and 44±18% (n=12, p=0.01), respectively. The amplitudes of inhibitory effects (changes between pre stim and during stim) were not different among PWs tested (p>0.05, one way ANOVA). Inhibition of BRC at PW of 0.12 ms of SNS was sustained for 10 min poststimulation (p=0.04, pre stim vs post stim, paired t test). The amplitudes of changes between pre stim and post stim were not different among PWs tested (p>0.05, one-way ANOVA).

In general, the results of the study showed that the chronaxie of the $T_{mot}$-PW curve was 0.04 ms, and that the stimulation charges/energies (current x PW) associated with shorter PWs of 0.02, 0.03, and 0.06 ms were significantly lower than those with longer PW (e.g., >0.15 ms). SNS ($T_{mot}$, 10 Hz) at selected PWs from 0.03 to 0.21 ms inhibited the frequency of BRCs. Further, there were no significantly different attenuations among tested PWs. SNS of PWs of 0.03, 0.06, and 0.09 ms decreased bladder contraction frequency from 103±3%, 100±4%, and 103±4% of controls, to 52±16% (n=8, p=0.02, paired t-test), 56±15% (n=11, p=0.02) and 40±19% (n=10, p=0.01), respectively.

The chronaxie of the L6 spinal nerve activation in the anesthetized rat of about 0.04 ms is much shorter than 0.1-0.21 ms typically used in previous preclinical and clinical studies. At fixed 10 Hz, $T_{mot}$ intensity, shorter PWs SNS are equally effective in attenuation of the frequency of bladder contractions as the longer PWs. Shorter PW neuromodulation may be advantageous due to potential decrease in battery-referred current consumption which subsequently, enhances device longevity. It may also reduce discomfort with short PW nerve stimulation due to higher nerve fiber selectivity compared to the 0.21 ms pulse-width that is widely used clinically.

For example, PW also affects the relative selectivity of stimulation among different types of nerve fibers (diameter). Shorter PWs will increase the differences in $T_{mot}$ from different diameters of nerve fibers. The average recruited nerve fiber diameter decreases (~20%) when the stimulus pulse-width increases from 0.01 ms to 1 ms. The threshold difference between large and small nerve fibers increases along with the increase in the relative distance between the stimulating electrode and the nerve fibers. Thus, preferential activation of large nerve fibers over small fibers can be more pronounced with a shorter PW stimulation especially when the electrode is placed farther from the nerve roots.

The spinal nerve is composed of a wide range of fiber types, including myelinated and Aβ fibers, as well as unmyelinated C-fibers. Inhibitory effects of SNS on bladder contractions may be stronger in rats pre-treated with capsaicin to desensitize C-fibers, and demonstrated that an activation of large fibers (without C-fibers) are associated with more effective neuromodulation of the bladder micturition reflex. Therefore, short PW SNS may increase fiber selectivity preferential to larger fibers and may translate to a reduced discomfort with short PW nerve stimulation.

Overall, the study identified the chronaxie (0.042 ms) of SNS evoked motor response and demonstrated effective BRC inhibitory effects between short and long PWs of SNS in a preclinical model. Potential battery savings manifested by shorter pulse-width while maintaining equivalent efficacy would provide more efficient therapy delivery and increased longevity of the stimulator.

The invention claimed is:
1. A method comprising:
  determining, using processing circuitry, a chronaxie of evoked threshold responses from electrical stimulation delivered to a nerve of a patient by at least:
    delivering, via a medical device, the electrical stimulation at a plurality of different pulse widths to the nerve;
    determining a threshold amplitude of the electrical stimulation that evokes a response at each respective pulse width of the plurality of pulse widths; and
    determining, using the processing circuitry, the chronaxie based on the respective threshold amplitudes and corresponding respective pulse widths of the plurality of pulse widths,
  wherein determining the chronaxie based on the respective threshold amplitudes and corresponding respective pulse widths of the plurality of pulse widths comprises determining the chronaxie based on a fit to $Y=(Y_0-N_S)*\exp^{(-K*X)}+N_S$, where Y is an evoked response, X is a pulse width, $Y_0$ is an initial value, $N_S$ is a rheobase, and K is an inverse of the chronaxie;
  receiving, using the processing circuitry, sensor data from a sensor; and
  initiating, based on the received sensor data, delivery of electrical stimulation having a pulse width at or near the determined chronaxie from the medical device to the nerve of a patient to treat a patient condition.

2. The method of claim 1, wherein the sensor data comprises first sensor data, the method further comprising:
  receiving, using the processing circuitry, second sensor data from the sensor; and
  suspending, based on the received second sensor data, the delivery of the electrical stimulation having the pulse width at or near the determined chronaxie from the medical device to the nerve of the patient.

3. The method of claim 2, wherein the second sensor data is indicative of the patient attempting to voluntarily void the at least one of the bladder or the bowel of the patient.

4. The method of claim 1, wherein the sensor data indicates an increase in a probability of an involuntary voiding of the at least one of the bladder or the bowel of the patient.

5. The method of claim 1, wherein the sensor includes one or more electrodes configured to sense afferent nerve signals, and wherein the sensor data includes the sensed afferent nerve signals.

6. The method of claim 1, wherein the sensor includes one or more electrodes configured to sense pudendal nerve signals, and wherein the sensor data includes the sensed pudendal nerve signals.

7. The method of claim 1, wherein the sensor includes one or more electrodes configured to sense electromyography (EMG) signals of a urinary sphincter of the patient, and wherein the sensor data includes the EMG signals.

8. The method of claim 1, wherein the sensor data includes data indicative of a pressure of the at least one of the bladder or the bowel of the patient.

9. The method of claim 1, wherein the sensor is configured to generate a signal that is indicative of at least one of patient activity level or patient posture state, and wherein the sensor data includes the signal indicative of the at least one of the patient activity level or the patient posture state.

10. The method of claim 1, wherein the received sensor data is indicative of a fill level of the bladder or the bowel of the patient, the method further comprising determining the fill level of the bladder or the bowel of the patient is above a threshold based on the received sensor data, wherein initiating, based on the received sensor data, the delivery of the electrical stimulation comprises initiating, based on the determination that the fill level of the bladder or the bowel of the patient is above the threshold, the delivery of the electrical stimulation.

11. The method of claim 1, further comprising detecting a voiding of the at least one of the bladder or the bowel of the patient based on the received sensor data, wherein initiating, based on the received sensor data, the delivery of the electrical stimulation comprises initiating, based on the detection of the voiding, the delivery of the electrical stimulation.

12. The method of claim 1, wherein the determining the chronaxie based on a fit to $Y=(Y_0-N_S)*\exp^{(-K*X)}+N_S$ comprises determining the chronaxie based on a non-linear fit to $Y=(Y_0-N_S)*\exp^{(-K*X)}+Ns$.

13. The method of claim 1, wherein:
  determining the chronaxie of evoked threshold responses from the electrical stimulation delivered to the nerve of the patient comprises determining the chronaxie of evoked threshold responses from the electrical stimulation delivered to a sacral nerve of the patient;
  delivering the electrical stimulation at the plurality of different pulse widths to the nerve comprises delivering the electrical stimulation at the plurality of different pulse widths to the sacral nerve of the patient; and
  initiating, based on the received sensor data, the delivery of the electrical stimulation having the pulse width at or near the determined chronaxie from the medical device to the nerve of the patient to treat the patient condition comprises initiating, based on the received sensor data, the delivery of the electrical stimulation having the pulse width at or near the determined chronaxie from the medical device to the sacral nerve of the patient to treat the patient condition.

14. The method of claim 1, wherein:
  determining the chronaxie of evoked threshold responses from the electrical stimulation delivered to the nerve of the patient comprises determining a chronaxie of evoked threshold motor responses from the electrical stimulation delivered to the nerve of the patient;
  determining the threshold amplitude of the electrical stimulation that evokes the response at each respective pulse width of the plurality of pulse widths comprises determining the threshold amplitude of the electrical stimulation that evokes a motor response at each respective pulse width of the plurality of pulse widths; and
  determining the chronaxie based on the fit to $Y=(Y_0-N_S)*\exp^{(-K*x)}+Ns$, where Y is the evoked response, X is the pulse width, $Y_0$ is the initial value, $N_S$ is the rheobase, and K is the inverse of the chronaxie comprises determining the chronaxie based on the fit to $Y=(Y_0-N_S)*\exp^{(-K*x)}+N_S$, where Y is an evoked motor response, X is the pulse width, $Y_0$ is the initial value, $N_S$ is the rheobase, and K is the inverse of the chronaxie.

15. The method of claim 1, wherein the sensor comprises an electrode on a lead, wherein initiating, based on the received sensor data, the delivery of the electrical stimulation having the pulse width at or near the determined chronaxie from the medical device to the nerve of the patient comprises initiating, based on the received sensor data, the delivery of the electrical stimulation via the electrode on the lead to the nerve of the patient.

16. The method of claim 1, wherein the delivered electrical stimulation to treat the patient condition is configured to inhibit contraction of at least one of a bladder or bowel of the patient.

17. A medical device system comprising:
  an electrical stimulation generator configured to deliver electrical stimulation to a nerve site of a patient; and
  processing circuitry configured to:
    determine a chronaxie of evoked threshold responses from electrical stimulation delivered to a nerve of a patient by at least:
      controlling the electrical stimulation generator to deliver the electrical stimulation at a plurality of different pulse widths to the nerve;
      determining a threshold amplitude of the electrical stimulation that evokes a response at each respective pulse width of the plurality of pulse widths; and
      determining the chronaxie based on the respective threshold amplitudes and corresponding respective pulse widths of the plurality of pulse widths by at least determining the chronaxie based on a fit to $Y=(Y_0-N_S)*\exp^{(-K*X)}+N_S$, where Y is an evoked response, X is a pulse width, $Y_0$ is an initial value, $N_S$ is a rheobase, and K is an inverse of the chronaxie, and
    receiving sensor data from a sensor; and
    control the electrical stimulation generator to initiate, based on the received sensor data, delivery of electrical stimulation having a pulse width at or near the determined chronaxie to the nerve of a patient to treat a patient condition.

18. The system of claim 17, wherein the sensor data comprises first sensor data, and wherein the processor is configured to:
receive second sensor data from the sensor; and
control the electrical stimulation generator to suspend, based on the received second sensor data, the delivery of the electrical stimulation therapy having the pulse width at or near the determined chronaxie to the nerve of the patient.

19. The system of claim 18, wherein the second sensor data is indicative of the patient attempting to voluntarily void the at least one of the bladder or the bowel of the patient.

20. The system of claim 17, wherein the sensor data indicates an increase in a probability of an involuntary voiding of the at least one of the bladder or the bowel of the patient.

21. The system of claim 17, wherein the sensor includes one or more electrodes configured to sense afferent nerve signals, and wherein the sensor data includes the sensed afferent nerve signals.

22. The system of claim 17, wherein the sensor includes one or more electrodes configured to sense pudendal nerve signals, and wherein the sensor data includes the sensed pudendal nerve signals.

23. The system of claim 17, wherein the sensor includes one or more electrodes configured to sense electromyography (EMG) signals of a urinary sphincter of the patient, and wherein the sensor data includes the EMG signals.

24. The system of claim 17, wherein the sensor data includes data indicative of a pressure of the at least one of the bladder or the bowel of the patient.

25. The system of claim 17, further comprising the sensor.

26. The system of claim 17, wherein the processing circuitry is configured to determine the chronaxie based on a non-linear fit to $Y=(Y_0-N_S)*\exp^{(-K*X)}+N_S$.

27. The system of claim 17, wherein the processing circuitry is configured to:
determine the chronaxie of evoked threshold responses from the electrical stimulation delivered to the sacral nerve of the patient;
control the electrical stimulation generator to deliver of the electrical stimulation at the plurality of different pulse widths to the sacral nerve of the patient; and
control the electrical stimulation generator to initiate, based on the received sensor data, the delivery of the electrical stimulation having the pulse width at or near the determined chronaxie from the medical device to the sacral nerve of the patient to treat the patient condition.

28. The system of claim 17, wherein the processing circuitry is configured to:
determine a chronaxie of evoked threshold motor responses from the electrical stimulation delivered to the nerve of the patient;
determine the threshold amplitude of the electrical stimulation that evokes a motor response at each respective pulse width of the plurality of pulse widths; and
determine the chronaxie based on the fit to $Y=(Y_0-N_S)*\exp^{(-K*X)}+N_S$, where Y is an evoked motor response, X is the pulse width, $Y_0$ is the initial value, $N_S$ is the rheobase, and K is the inverse of the chronaxie.

29. The system of claim 17, further comprising the sensor, wherein the sensor comprises an electrode on a lead, wherein the processing circuitry is configured to control the electrical stimulation generator to initiate, based on the received sensor data, the delivery of the electrical stimulation having the pulse width at or near the determined chronaxie via the electrode on the lead to the nerve of the patient.

30. The system of claim 17, wherein the delivered electrical stimulation to treat the patient condition is configured to inhibit contraction of at least one of a bladder or bowel of the patient.

* * * * *